United States Patent
Bitziou et al.

(10) Patent No.: US 10,290,385 B2
(45) Date of Patent: May 14, 2019

(54) SYNTHETIC DIAMOND MATERIALS FOR ELECTROCHEMICAL SENSING APPLICATIONS

(71) Applicant: Element Six Technologies Limited, Oxfordshire (GB)

(72) Inventors: Eleni Bitziou, West Midlands (GB); Laura Anne Hutton, Oxfordshire (GB); Julie Victoria MacPherson, West Midlands (GB); Mark Edward Newton, West Midlands (GB); Patrick Robert Unwin, West Midlands (GB); Nicola Louise Palmer, Oxfordshire (GB); Timothy Peter Mollart, Oxfordshire (GB); Joseph Michael Dodson, Berkshire (GB)

(73) Assignee: Element Six Limited (IM)

( * ) Notice: Subject to any disclaimer, the term of this patent is extended or adjusted under 35 U.S.C. 154(b) by 82 days.

(21) Appl. No.: 14/382,464

(22) PCT Filed: Mar. 13, 2013

(86) PCT No.: PCT/EP2013/055170
§ 371 (c)(1),
(2) Date: Sep. 2, 2014

(87) PCT Pub. No.: WO2013/135783
PCT Pub. Date: Sep. 19, 2013

(65) Prior Publication Data
US 2015/0102266 A1    Apr. 16, 2015

Related U.S. Application Data

(60) Provisional application No. 61/610,286, filed on Mar. 13, 2012.

(30) Foreign Application Priority Data

Mar. 13, 2012    (GB) .................................. 1204388.1

(51) Int. Cl.
*H01B 1/04*      (2006.01)
*G01N 27/30*     (2006.01)

(52) U.S. Cl.
CPC ............. *H01B 1/04* (2013.01); *G01N 27/308* (2013.01)

(58) Field of Classification Search
None
See application file for complete search history.

(56) References Cited

U.S. PATENT DOCUMENTS

| 5,371,378 A | 12/1994 | Kalyankumar | |
|---|---|---|---|
| 2011/0210004 A1* | 9/2011 | Unwin | C04B 41/009 205/50 |
| 2012/0286289 A1* | 11/2012 | Dipalo | G01N 27/414 257/77 |

FOREIGN PATENT DOCUMENTS

| GB | 2486778 A | 6/2012 |
|---|---|---|
| JP | 2010516600 A | 5/2010 |

(Continued)

OTHER PUBLICATIONS

International Search Report for PCT/EP2013/055170 dated Jun. 7, 2013.

(Continued)

*Primary Examiner* — Guinever S Gregorio
(74) *Attorney, Agent, or Firm* — Armstrong Teasdale LLP

(57) ABSTRACT

A boron doped synthetic diamond material which has the following characteristics: a solvent window meeting one or both of the following criteria as measured by sweeping a potential of the boron doped synthetic diamond material (Continued)

with respect to a saturated calomel reference electrode in a solution containing only deionized water and 0.1M $KNO_3$ as a supporting electrolyte at pH 6: the solvent window extends over a potential range of at least 4.1 V wherein end points of the potential range for the solvent window are defined when anodic and cathodic current density measured at the boron doped synthetic diamond material reaches 38 mA $cm^{-2}$; and the solvent window extends over a potential range of at least 3.3 V wherein end points of the potential range for the solvent window are defined when anodic and cathodic current density measured at the boron doped synthetic diamond material reaches 0.4 mA $cm^{-2}$; a peak-to-peak separation $\Delta Ep$ (for a macroelectrode) or a quartile potential $\Delta E_{3/4\_1/4}$ (for a microelectrode) of no more than 70 mV as measured by sweeping a potential of the boron doped synthetic diamond material at a rate of 100 mV $s^{-1}$ with respect to a saturated calomel reference electrode in a solution containing only deionized water, 0.1M KNO3 supporting electrolyte, and 1 mM of $FcTMA^+$ or $Ru(NH_3)_6^{3+}$ at pH 6; and a capacitance of no more than 10 µF $cm^{-2}$ as measured by sweeping a potential of the boron doped synthetic diamond material with respect to a saturated calomel reference electrode between 70 mV and −70 mV in a solution containing only deionized water and 0.1M $KNO_3$ supporting electrolyte at pH 6, measuring resultant current, subtracting a current value at 0 V when sweeping towards negative potentials from a current value at 0 V when sweeping towards positive potentials, dividing the subtracted current value by 2, and then dividing the result by an area ($cm^2$) of the boron doped synthetic diamond material and by a rate at which the potential is swept ($Vs^{-1}$) to give a value for capacitance in F $cm^{-2}$.

14 Claims, 19 Drawing Sheets

(56) References Cited

FOREIGN PATENT DOCUMENTS

| | | |
|---|---|---|
| WO | 2006/013430 A | 2/2006 |
| WO | 2007/107844 A1 | 9/2007 |
| WO | 2008090510 A1 | 7/2008 |

OTHER PUBLICATIONS

International Search Report for GB1204388.1 dated Jul. 6, 2012.
Wilson, et al., "Impact of grain-dependent boron uptake on the electrochemical and electrical properties of polycrystalline boron doped diamond electrodes", Journal of Physical Chemistry B 110, pp. 5639-5646, 2006.
Martin et al., "Hydrogen and oxygen evolution on boron-doped diamond electrodes", Journal of Electrochemical Society 143(6), L133-136, 1996.
Gao, "Preparation and characteristic measurement of born doped diamond film electrode on tantalum substrate and its properties for degradation of high COD wastewater", Applied Mechanics and Materials, 138-139, 612-617, 2012.
International Search Report for GB1304503.4 dated Aug. 21, 2013.
Bouamrane et al., "Underpotential Deposition of Cu on boron-doped diamond thin films", J. Phys. Chem. B102, Jan. 1, 1998.
Pihel, et al., "Overoxidized Polypyrrole-coated carbon fiber microelectrodes for dopamine measurements with fast-scan cyclic voltammetry", Anal. chem. 168, 1996, pp. 2084-2089.
Del Campo et al., "Voltammetry at Boron-Doped Diamond Electrodes in Liquid Ammonia: Solvent Window Effects and Diamond Surface Modification", Electrochemical and Solid-State Letters 3 (5), Jan. 1, 2000, 224.
Granger, et al., "The influence of surface interactions on the reversibility of ferri/ferrocyanide at boron-doped diamond thin-film electrodes", Journal of the Electrochemical Society, 1999, 146 (12) pp. 4551-4558.
Colley, et al., "Examination of the Spatially Heterogeneous Electroactivity of Boron-Doped Diamond Microarray Electrodes", Analytical Chemistry, vol. 78, No. 8, pp. 2539-2548, Apr. 1, 2006.
Achard et al., "Thick boron doped diamond single crystals for high power electroni cs", Diamond and Related Materials, 20, 2011, 145-152.
Kondo et al., "Homoepitaxial single-crystal boron-doped diamond electrodes for electroanalysis", Journal of the Electrochemical Society, vol. 149, No. 6, pp. E179-E184, Jun. 1, 2002.
Coffinier et al., "Covalent linking of peptides onto oxygen-terminated boron-doped diamond surfaces", Diamond and Related Materials Elsevier Science Publishers, vol. 16 , No. 4-7, Apr. 13, 2007.
Kraft, A., "Doped diamond: a compact review on a new, versatile electrode material", Int. J. Electrochem. Sci. 2007, 2, 355.
Luong, et al., "Boron-doped diamond electrode: synthesis, characterization, functionalization and analytical application", Analyst 2009, 134, 1965-1979.
Compton, R. G., "Electroanalysis at diamond-like and doped-diamond electrodes", Electroanalysis 2003, 15, No. 17, p. 1349.
Liu, et al., "Conductivity detection for monitoring mixing reactions in microfluidic devices", Analyst, 2001, 126, pp. 1248-1251.
Pleskov, Y. V., "Electrochemistry of diamond: a review", Russ. J. Electrochem. 2002, 38, 1275.
Xu et al., "Boron-doped diamond thin-film electrodes", Anal. Chem. 1997, 69, A591.
Alehashem et al., "Cyclic Voltammetric studies of charger transfer reaction at highly boron-doped polycrystalline diamond thin-film electrodes", Anal. Chem. 1995, 67, 2812.
Sze, et al., "Semiconductor device development in the 1970s and 1980's—a perspective", Proceedings of the IEEE, vol. 69, No. 9, p. 1121.
Angus, et al., "Conducting diamond electrodes: application in electrochemistry", N. New Diamond Front. Carbon Technol. 1999, 9, 175.
Granger, et al., "Standard electrochemical behavior of high-quality, boron-doped polycrystalline diamond thin-film electrodes", Anal. Chem., 72, pp. 3793-3804, 2000.
Yagi, et al., "Electrochemical selectivity for redox systems at oxygen-terminated diamond electrodes", A. J. Electroanal. Chem. 1999, 473, 173.
Wu, et al., "Nickel oxide/hydroxide nanoplatelets synthesized by chemical precipitation for electrochemical capacitors", Electrochim. Acta 2008, 53, 3427.
Gerischer, "Semiconductor electrochemistry", Physical Chemistry, An Advanced Treatise, Ed.; Academic Press, New York, 1970, pp. 463-542.
Marcus, R. A., "On the theory of oxidation-reduction reactions involving electron transfer", The Journal of Chemical Physics 1956, 24, 966.
Tenne, et al., "Efficient electrochemical reduction of nitrate to ammonia using conductive diamond film electrodes", J. Electroanal. Chem. 1993, 347, 409.
Shakkthivel, et al., "Simultaneous determination of ascorbic acid and dopamine in the presence of uric acid on ruthenium oxide modified electorde", Biosens. Bioelectron. 2007, 22, 1680.
Boukherroub, R., et al., "Photochemical oxidation of hydrogenated boron-doped diamond surfaces", Electrochem. Commun. 2005, 7, 937.
Actis, P., et al., "Influence of the surface termination on the elctrochemical properties of boron-doped diamond (BDD) interfaces", Electrochem. Commun. 2008, 10, 402.
Marken, F., et al., "Direct cytochrome c electrochemistry at boron-doped diaond electrodes", Electrochem. Commun. 2002, 4, 62.
Prado, C., et al., "Simultaneous electrochemical detectiona nd determination of lead and copper at boron-doped diamond film electordes", Electroanalysis 2002, 14, 262.

(56) References Cited

OTHER PUBLICATIONS

El Tall, O., et al., "Anodic stripping voltammetry of heavy metals at nanocrystalline boron-doped diamond electrode", Electroanalysis 2007, 19, 1152.
McEvoy, et al., "Direct electrochemistry of blue copper proteins at boron-doped diamond electrodes", Electrochim. Acta 2005, 50, 2933.
Ristein, J., "Structural and electronic properties of diamond surfaces", Thin-Film Diamond II; Elsevier Academic Press, 2004; vol. 77, p. 37-96.
Ohnishi, K., et al., "Electrochemical glucose detection using nickel-implanted boron-doped diamond electrodes", Electrochem. Solid-State Lett. 2002, 5, D1.
Lawrence et al., "Amperometric detection of sulfide at a born doped diamond electrode: the electrocatalytic reaction of sulfide with ferricyanide in aqueous solution", Electroanalysis, 2002, 14(7-8), 499-504.
Bouamrane, F. et al, "Electrochemcal study of diamond thin films in neutral and basic solutions of nitrate", Journal of Electroanalytical Chemistry, Apr. 12, 1996, vol. 405, Nos. 1-2, p. 95-99.
Bennett et al. "Effect of sp(sup 2)-Bonded Nondiamond Carbon Impurity on the Response of Boron-Doped Polycrystalline Diamond Thin-Film Electrodes", Journal of the Electrochemical Society,vol. 151,No. 9, Jan. 1, 2004, p. E306, XP055289912, ISSN: 0013-4651, DOI:10.1149/1.1780111.
European Exam Report for European Application No. 13712177.8, dated Jul. 25, 2016 (5 pages).

\* cited by examiner

SYNTHETIC DIAMOND MATERIALS FOR ELECTROCHEMICAL SENSING APPLICATIONS

CROSS-REFERENCE TO RELATED APPLICATIONS

This application is the national stage entry under 35 U.S.C. § 371 of PCT/EP2013/055170 filed on 13 Mar. 2013, which claims priority to U.S. Provisional Application 61/610,286 filed on 13 Mar. 2012 and UK application 1204388.1 filed on 13 Mar. 2012, all of which are incorporated by reference in their entirety.

FIELD OF INVENTION

The present invention relates to synthetic diamond materials suitable for electrochemical sensing applications.

BACKGROUND OF INVENTION

Boron doped synthetic diamond materials, both single crystal and polycrystalline, have been the subject of considerable interest as electrode materials, with review articles focusing on their many applications from electroanalysis to bulk electrolysis. A wide potential window in aqueous solution, low background currents, and resistance to fouling make boron doped diamond materials particularly attractive for use in electroanalysis. Boron doped synthetic diamond materials are also resistant to corrosion under both acidic and alkaline conditions, as well as at extreme positive and negative applied potentials, and are stable at high temperatures and pressures. Useful background information can be found in the following papers: Kraft, A. *Int. J. Electrochem. Sci.* 2007, 2, 355; Luong, J. H. T.; Male, K. B.; Glennon, J. D. *Analyst* 2010, 135, 3008; Compton, R. G.; Foord, J. S.; Marken, F. *Electroanalysis* 2003, 15, 1349; Liu, Y.; Wipf, D. O.; Henry, C. S. *Analyst* 2001, 126, 1248; Pleskov, Y. V. *Russ. J. Electrochem.* 2002, 38, 1275; Xu, J. S.; Granger, M. C.; Chen, Q. Y.; Strojek, J. W.; Lister, T. E.; Swain, G. M. *Anal. Chem.* 1997, 69, A591; Sze, S. M. *Proceedings of the IEEE* 1981, 69, 1121; Alehashem, S.; Chambers, F.; Strojek, J. W.; Swain, G. M.; Ramesham, R. *Anal. Chem.* 1995, 67, 2812; Angus, J. C.; Martin, H. B.; Landau, U.; Evstefeeva, Y. E.; Miller, B.; Vinokur, N. *New Diamond Front. Carbon Technol.* 1999, 9, 175; Granger, M. C.; Swain, G. M. *J. Electrochem. Soc.* 1999, 146, 4551; Granger, M. C.; Witek, M.; Xu, J. S.; Wang, J.; Hupert, M.; Hanks, A.; Koppang, M. D.; Butler, J. E.; Lucazeau, G.; Mermoux, M.; Strojek, J. W.; Swain, G. M. *Anal. Chem.* 2000, 72, 3793; Yagi, I.; Notsu, H.; Kondo, T.; Tryk, D. A.; Fujishima, A. *J. Electroanal. Chem.* 1999, 473, 173; and Wu, M.-S.; Hsieh, H.-H. *Electrochim. Acta* 2008, 53, 3427.

While early papers summarised research on the basic electrochemical properties of boron doped synthetic diamond materials, the results have been found to differ greatly depending on the diamond sample used, as well as the experimental set-up and electrical contact.

The present inventors have systematically investigated how material characteristics of boron doped diamond materials affect the electrochemical properties and then developed new materials which are optimized for their electrochemical performance.

SUMMARY OF INVENTION

According to a first aspect of the present invention there is provided a boron doped synthetic diamond material which has the following characteristics:

a solvent window meeting one or both of the following criteria as measured by sweeping a potential of the boron doped synthetic diamond material with respect to a saturated calomel reference electrode in a solution containing only deionised water and 0.1M $KNO_3$ as a supporting electrolyte at pH 6:
  the solvent window extends over a potential range of at least 4.1 V wherein end points of the potential range for the solvent window are defined when anodic and cathodic current density measured at the boron doped synthetic diamond material reaches 38 mA $cm^{-2}$; and
  the solvent window extends over a potential range of at least 3.3 V wherein end points of the potential range for the solvent window are defined when anodic and cathodic current density measured at the boron doped synthetic diamond material reaches 0.4 mA $cm^2$;

a peak-to-peak separation $\Delta E_p$ (for a macroelectrode) or a quartile potential $\Delta E_{3/4-1/4}$ (for a microelectrode) of no more than 70 mV as measured by sweeping a potential of the boron doped synthetic diamond material at a rate of 100 mV $s^{-1}$ with respect to a saturated calomel reference electrode in a solution containing only deionised water, 0.1M $KNO_3$ supporting electrolyte, and 1 mM of $FcTMA^+$ or $Ru(NH_3)_6^{3+}$ at pH 6; and a capacitance of no more than 10 $\mu F$ $cm^{-2}$ as measured by sweeping a potential of the boron doped synthetic diamond material with respect to a saturated calomel reference electrode between 70 mV and −70 mV in a solution containing only deionised water and 0.1M $KNO_3$ supporting electrolyte at pH 6, measuring resultant current, subtracting a current value at 0 V when sweeping towards negative potentials from a current value at 0 V when sweeping towards positive potentials, dividing the subtracted current value by 2, and then dividing the result by an area ($cm^2$) of the boron doped synthetic diamond material and by a rate at which the potential is swept ($Vs^{-1}$) to give a value for capacitance in F $cm^{-2}$.

Embodiments of the present invention are directed to synthetic diamond materials suitable for electrochemical sensing applications. These include both polycrystalline (pBDD) and single crystal (scBDD) boron doped synthetic diamond materials. The synthetic diamond materials described herein have been optimized for their electrochemical sensing performance which is believed to exceed all previous comparable materials. That said, it is also envisaged that such materials may be useful in other applications such as electrodes for electrochemical processing (e.g. to electrochemically treat solutions such as in water treatment processes as distinct from electrochemically sensing target species within a solution) and electronic device applications where highly conductive synthetic diamond materials are useful.

In addition to the above, certain further embodiments relate to electrochemical sensing devices incorporating such materials and electrochemical sensing methods which utilize such electrochemical sensing devices to sense target species at a level of sensitivity which is believed to exceed all previous comparable devices and sensing methods.

BRIEF DESCRIPTION OF THE DRAWINGS

For a better understanding of the present invention and to show how the same may be carried into effect, embodiments of the present invention will now be described by way of example only with reference to the accompanying drawings, in which:

FIG. 14(b) shows a cross sectional plot of $k^0$ illustrating the variation in $k^0$ both within a single grain and across grains;

DETAILED DESCRIPTION OF EMBODIMENTS

Figure 1:
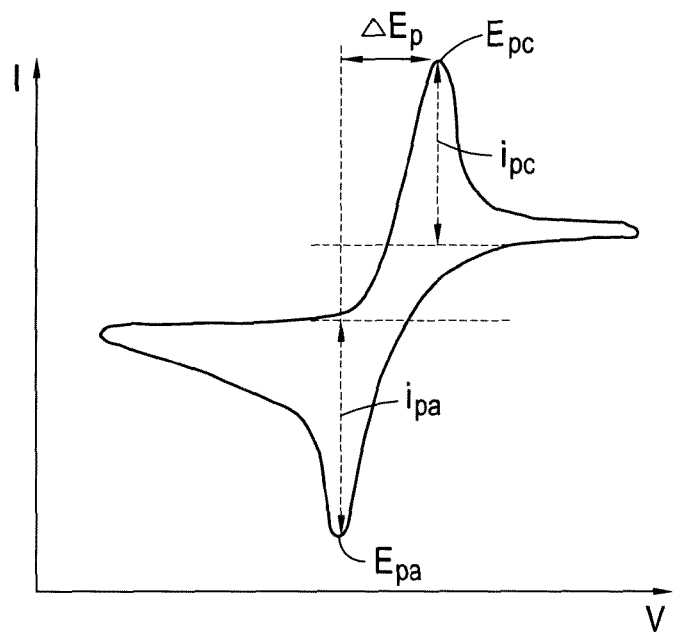
FIG. 1 illustrates a typical cyclic voltammogram for a macroelectrode with oxidation and reduction peaks separated by a peak-to-peak potential, $\Delta Ep$.

Voltammetric and amperometric sensing comprises applying a potential to a sensing electrode (relative to a reference electrode) so as to cause an electrochemical reaction to occur at the surface of the sensing electrode and measuring a current which results from the electrochemical reaction. Typically results are presented as a voltammogram. For example, a typical cyclic voltammogram is indicated in FIG. 1 which comprises a plot of current (I) versus potential (V) as the sensing electrode is scanned over a potential range. The cyclic voltammogram comprising a reduction peak $i_{pc}$ at a potential $E_{pc}$ and an oxidation peak $i_{pa}$ at a potential $E_{pa}$ corresponding to a reduction reaction and an associated oxidation reaction of a redox active species within a solution being analysed.

A reversible reaction is one where the electron transfer kinetics between the electrode and redox species in solution are so fast (compared to the mass transport characteristics of the system) that the concentration of species at the electrode surface are maintained at equilibrium conditions and are related via the Nernst equation. The process is termed mass transport controlled and normally it is only required to consider diffusion, i.e. diffusion controlled. Supporting electrolyte is added to suppress migration and the solution can be kept under quiescent conditions, i.e. no need to consider convection.

The separation between the potential of the anodic and cathodic peak currents, i.e. the peak to peak potential $\Delta E_p$, is often used as a diagnostic for reversibility of a system. For classic metal macrodisk electrodes, under quiescent only conditions, mass transport (diffusion) will limit the rate of an electrochemical fast outer sphere electron transfer process leading to a reversible response. Outer sphere electron transfer is when the redox analyte of interest does not need to interact with the surface of the substrate in order to transfer electrons. For a reversible species at a metal electrode, this separation is close to 2.3 RT/nF (59/n for 25° C.), where R is the molar gas constant, T is temperature, n is the apparent number of electrons transferred, and F is the Faraday constant. As such, an ideal electrode material will thus be one which has a $\Delta Ep$ of approximately 59 mV for a single electron process at 25° C.

Figure 2:
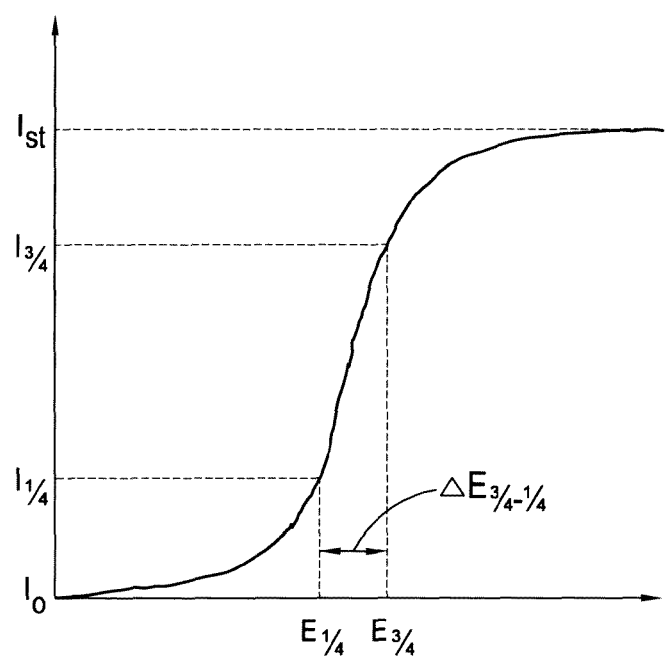
FIG. 2 illustrates a typical voltammogram trace for a microelectrode showing a quartile potential, $\Delta E_{3/4-1/4}$.

The aforementioned discussion relates to macroelectrodes which typically have all working surface length dimensions greater than 100 μm. As described, a typical cyclic voltammogram obtain using such an electrode comprises oxidation and reduction peaks and the condition for reversibility for a macroelectrode can be obtained by measuring the peak to peak separation $\Delta Ep$. In contrast, a microelectrode is one which has at least one length dimension across its working surface of equal to or less 100 μm. A microelectrode typically has a diffusion rate which is much higher than for a macroelectrode and oxidation and reduction peak are not observed. Instead the current attains a steady-state response at an appropriate potential. Here, conditions for reversibility can be obtained by analysing the slope of the current-voltage curve as the current transitions from zero current to a maximum steady state current. In particular, a voltage ($E_{1/4}$) can be measured when the current ($I_{1/4}$) is ¼ its steady state value ($I_{ss}$) and a voltage ($E_{3/4}$) can be measured when the current ($I_{3/4}$) is ¾ its steady state value. The quartile potential $\Delta E_{3/4-1/4}$ is obtained by subtracting $E_{1/4}$ from $E_{3/4}$ (i.e. $\Delta E_{3/4-1/4} = |E_{3/4} - E_{1/4}|$). A typical voltammogram trace for a microelectrode is illustrated in FIG. 2 showing how $\Delta E_{3/4-1/4}$ is obtained. As with $\Delta Ep$ for macroelectrodes, for microelectrodes if $\Delta E_{3/4-1/4}$ approaches 59 mV for a 1 electron transfer process the reaction is deemed reversible. The discussion below largely refers to macroelectrodes and the peak-to-peak separation $\Delta Ep$. However, it should be understood that the same comments apply equally well to microelectrodes and the quartile potential $\Delta E_{3/4-1/4}$.

Figure 3A:
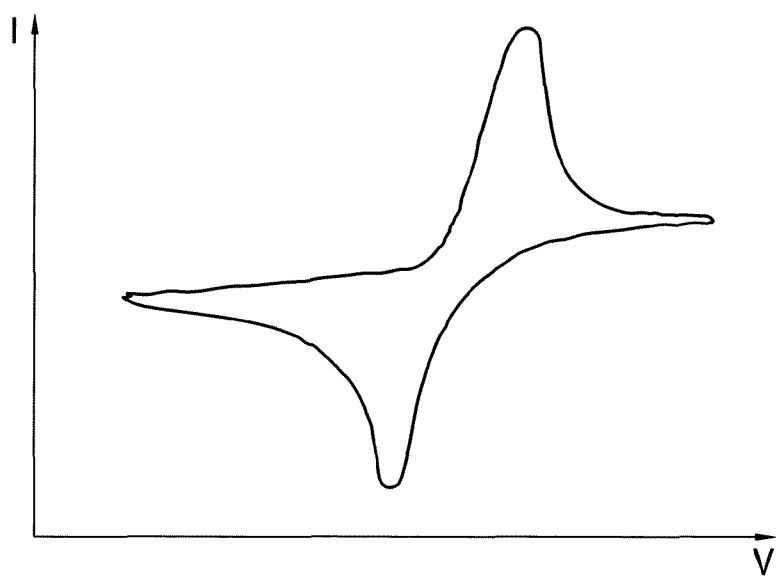
FIG. 3 illustrates how a cyclic voltammogram varies between: (a) one which has relative narrow, well defined oxidation and reduction peaks with a small $\Delta Ep$; and (b) one which has relatively broad oxidation and reduction peaks with a large $\Delta Ep$.
Figure 3B:
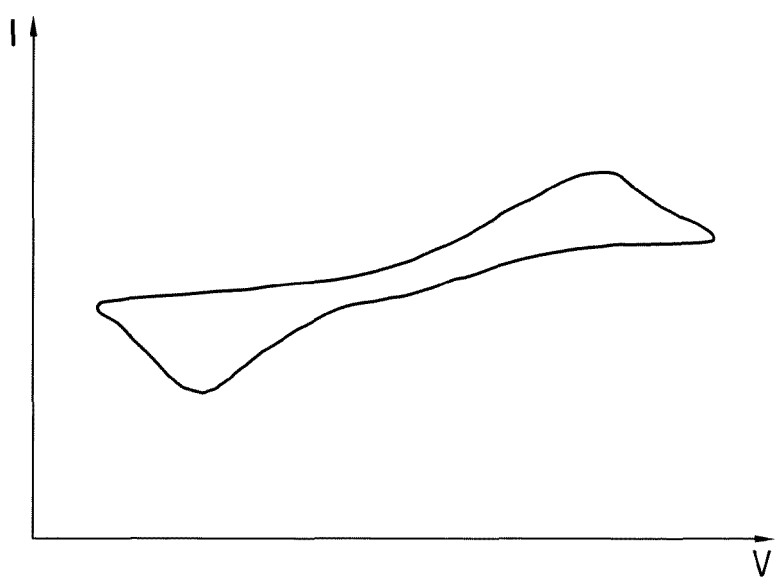

FIG. 3 illustrates how a cyclic voltammogram varies between: (a) one which has relative narrow, well defined oxidation and reduction peaks with a small $\Delta Ep$; and (b) one which has relatively broad oxidation and reduction peaks with a large $\Delta Ep$. For a fast electron transfer outer sphere redox couple, in the situation where an electrode material is selected which results in relatively broad oxidation and reduction peaks with a large $\Delta Ep$ the sensitivity and selectivity of this material to detect a range of different analytes in a solution is detrimentally affected.

In addition to the above, to enhance sensitivity it is desirable that an electrode material provides a flat baseline response to enhance signal to noise ratio and thus sensitivity to detect an analyte. Desirable features to providing a wide, flat baseline include a large solvent window, a flat electrochemical response, and a low capacitance.

Figure 4A:
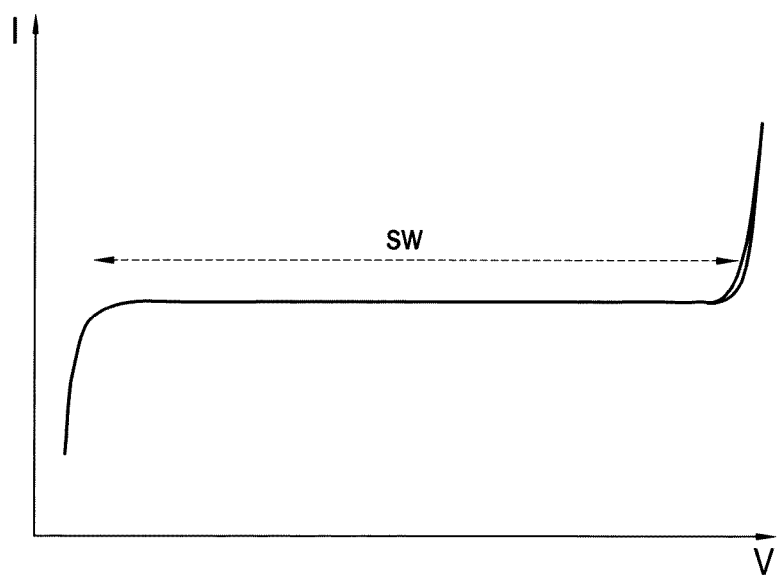
FIG. 4 illustrates how a cyclic voltammogram varies for deionised water, containing supporting electrolyte, between: (a) an electrode material which has a broad solvent window SW; and (b) an electrode material which has a narrow solvent window SW.
Figure 4B:
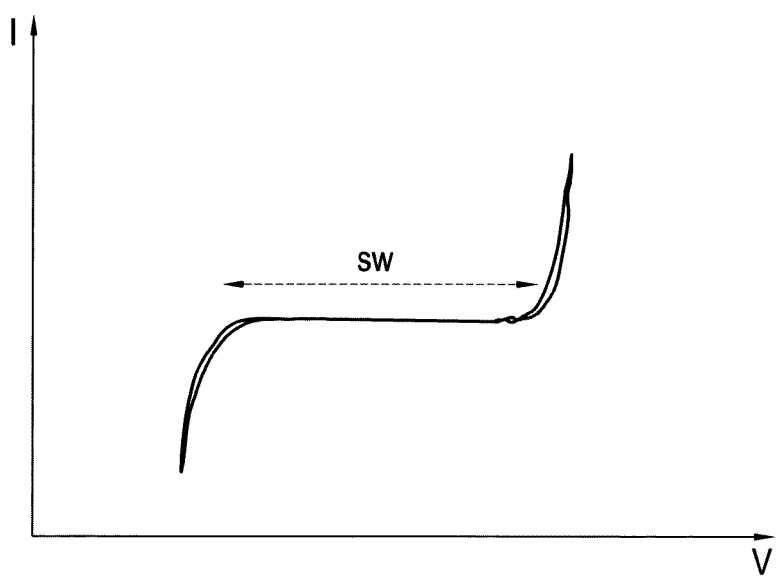

The solvent window is defined by the potential limits at which the solvent, typically water or supporting electrolyte, is oxidized or reduced causing large currents to flow. As such, the solvent window defines the useful potential range over which electrochemical sensing can be performed. Different electrode materials have different solvent windows and thus it is desirable to select a material which has a large solvent window to maximize the number of species which can be electrochemically sensed within the solvent window. FIG. 4 illustrates how a cyclic voltammogram varies for deionised water containing supporting electrolyte between:

(a) an electrode material which has a broad solvent window; and (b) an electrode material which has a narrow solvent window.

Within the solvent window it is also desirable that an electrode material exhibits a flat response to enhance the signal (faradaic) to noise (non-faradaic) ratio within the working range. Factors such as oxidation/reduction of the electrode material itself and double layer charging, i.e. capacitance, all affect the non-faradaic current. For example, this can be a big problem with metal electrodes as metals can readily be oxidized and subsequently a metal oxide surface reduced. This is less of a problem for boron doped diamond materials. However, any sp2 carbon in a surface layer of the boron doped diamond material can be oxidized and reduced and thus be problematic.

The measured capacitance is the function of several contributing factors given by the equation:

$$C_{measured}^{-1} = C_H^{-1} + C_{sc}^{-1} + C_{diff}^{-1}$$

where $C_{measured}$ is the capacitance value measured experimentally, $C_H$ is the capacitance of the Helmholtz double layer (20 µF cm$^{-2}$), $C_{sc}$ is the space charge capacitance of the boron doped synthetic diamond electrode, and $C_{diff}$ is the capacitance of the diffuse double layer (where in 0.1M electrolyte, $C_{diff} \gg C_H$).

Figure 5A:
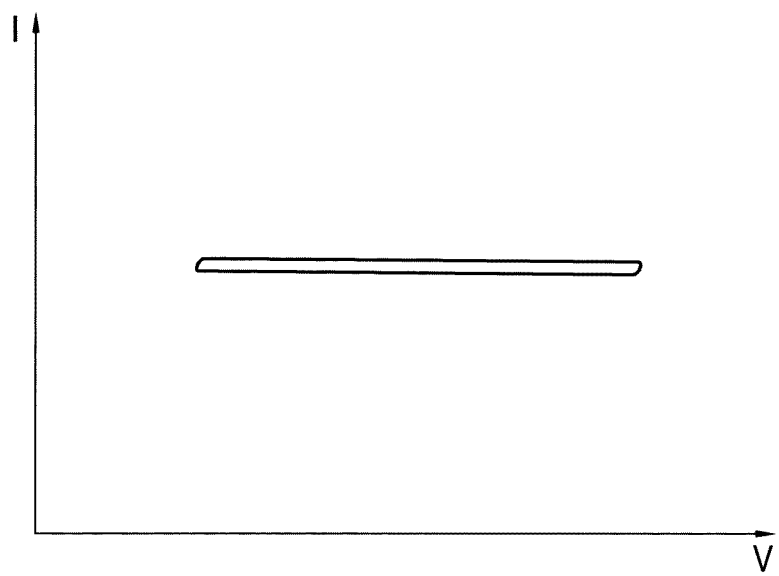
FIG. 5 illustrates how the baseline response of a cyclic voltammogram varies between: (a) an electrode material which exhibits a low capacitance; and (b) an electrode material which exhibits a high capacitance.
Figure 5B:
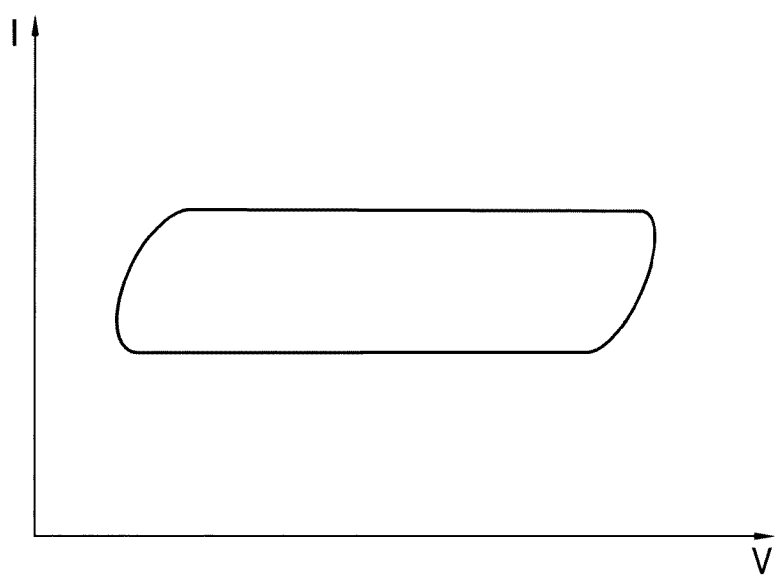

FIG. 5 illustrates how the baseline response of a cyclic voltammogram varies between: (a) an electrode material which exhibits a low capacitance; and (b) an electrode material which exhibits a high capacitance. Both are assumed to show negligible surface oxidation/reduction processes. As illustrated, increasing the capacitance increases the baseline for both oxidation and reduction thus reducing sensitivity to detect an analyte of interest. Accordingly, an electrode with a low capacitance is desirable. Further still, variations in the composition of an electrode can result in variations in the electrochemical response of an electrode across its solvent window which is also undesirable.

For boron doped diamond materials, a low boron dopant content can aid in providing a large solvent window, flat electrochemical response, and low capacitance as desired. However, such material will not show metallic like properties resulting in non-reversible electrochemical characteristics for simple fast electron transfer outer sphere redox couples in the both positive and negative potential windows and is thus not desirable for electrochemical sensing applications. Increasing the boron dopant content significantly will cause the solvent window to shrink and the capacitance to increase, which is undesirable for the aforementioned reasons. As such, it has been found that an optimum range of boron concentration exists which balances the requirement of reversible electrochemistry for simple fast electron transfer outer sphere redox couples versus the desirable characteristics of a large solvent window, a flat electrochemical response, and a low capacitance.

In addition to the above, it has been found that sp2 carbon content within the boron doped diamond material is undesirable as this also tends to shrink the solvent window, increase capacitance, and increase non-uniformities in the electrochemical response of the electrode material. If the boron dopant content becomes too high then it is more difficult to control the presence of non-diamond carbon, e.g. sp2 carbon, providing an additive detrimental effect on the performance of the electrode material in terms of providing a wide, flat baseline for species detection.

The present inventors have developed polycrystalline CVD synthetic diamond materials and single crystal CVD diamond materials which have optimized boron concentrations and substantially no sp2 carbon (as detectable via Raman spectroscopy). As such, it has been found to be possible to provide boron doped synthetic diamond materials with the following characteristics:

a solvent window (as measured under conditions of 0.1M KNO$_3$ at pH 6 versus an SCE reference electrode) meeting one or both of the following criteria: (i) extending over at least a potential range of 4.1 V, 4.2 V, 4.3 V, 4.5 V, 4.6 V, or 4.7 V wherein end points of the potential range for the solvent window are defined when anodic and cathodic current density measured at the boron doped synthetic diamond material reaches 38 mA cm$^{-2}$; (ii) extending over at least a potential range of 3.3 V, 3.4 V, 3.5 V, or 3.6 V wherein end points of the potential range for the solvent window are defined when anodic and cathodic current density measured at the boron doped synthetic diamond material reaches 0.4 mA cm$^{-2}$;

a $\Delta E_p$ (macroelectrode) or $\Delta E_{3/4-1/4}$ (microelectrode) of no more than 70 mV, 68 mV, 66 mV, 64 mV, 62 mV, 60 mV or 59 mV for fast electron transfer one electron outer sphere redox couples in both a positive and negative potential window; and a measured capacitance of less than 10 µF cm$^{-2}$, 8 µF cm$^{-2}$, 6 µF cm$^{-2}$, 5 µF cm$^{-2}$, 4 µF cm$^{-2}$, 3 µF cm$^{-2}$, 2 µF cm$^{-2}$, or 1 µF cm$^{-2}$.

While it has previously been demonstrated that a boron doped synthetic diamond material can fulfill one or two of these desirable parameters (e.g. a wide solvent window and a low capacitance but with a large $\Delta E_p$, or alternatively a low $\Delta E_p$ but a narrower solvent window and a higher capacitance) it has been recognized that all three requirements are desired to achieve electrochemical sensing with optimized selectivity and sensitivity and it is believed that the materials of the present invention are the first to achieve all these desirable characteristics in combination.

It is also important to note that the value of the aforementioned electrochemical parameters can vary according to the manner in which the parameters are measured. The aforementioned values correspond to those obtained using specific measurement techniques as defined below.

The solvent window is measured by sweeping the potential of a boron doped synthetic diamond electrode with respect to a reference electrode in a solution containing only solvent (deionised water) and 0.1M supporting electrolyte (KNO$_3$). According to one option the end points of the stated potential range for the solvent window are defined when anodic and cathodic current density measured at the boron doped synthetic diamond electrode material reaches 38 mA cm$^{-2}$. For example, embodiments may have a solvent window extending over at least a potential range of -2.0V to +2.1V, -2.1V to +2.2V, -2.1V to +2.3V, -2.2V to +2.3V, -2.2V to +2.4V, or -2.3V to +2.4V measured in this way. According to an additional or alternative option the end points of the stated potential range for the solvent window are defined when anodic and cathodic current density measured at the boron doped synthetic diamond electrode material reaches 0.4 mA cm$^{-2}$. In this case the solvent window will be defined to be a little narrower. Preferably boron doped synthetic diamond material according to the present invention meets both the solvent window definitions although for certain applications it may only be required to meet one of the solvent window definitions. For example, for electrochemical processes which are located in a more central region of the solvent window then the important criteria will be flatness of the window over the central region while for electrochemical processes which are located in a more peripheral region of the solvent window then the important criteria will be the peripheral extent of the solvent window.

$\Delta E_p$ (macroelectrode) or $\Delta E_{3/4-1/4}$ (microelectrode) is measured by sweeping a potential of the boron doped synthetic diamond material at a rate of 100 mV s$^{-1}$ with respect to a saturated calomel reference electrode in a solution containing only deionised water, 0.1M KNO$_3$ supporting electrolyte, and 1 mM of FcTMA$^+$ or Ru(NH$_3$)$_6$$^{3+}$ at pH 6.

The capacitance is measured by sweeping the potential of a boron doped synthetic diamond electrode with respect to a reference electrode between 70 mV and −70 mV in a solution containing solvent (deionised water) and 0.1M supporting electrolyte (KNO$_3$). The resulting current at the boron doped synthetic diamond electrode is measured. The current at 0 V when sweeping towards negative potentials is subtracted from the current at 0 V when sweeping towards positive potentials and divided by 2. This current is then divided by the area (cm$^2$) of the boron doped synthetic diamond electrode and by the rate at which the potential is swept (Vs$^{-1}$) to give the value for capacitance in F cm$^{-2}$.

It should be noted that while the boron doped synthetic diamond materials of the present invention have been characterized in aqueous solution as outlined above, it is envisaged that the materials may be used in other types of solution (e.g. including organic solvents). As such, it will be understood that the characterisation of the materials is not intended to limit the use of the materials in a range of applications.

The boron doped synthetic diamond materials have been defined above in terms of their functional electrochemical properties as this is the most convenient, clear, and concise way to characterize the materials. In practice, the present inventors have fabricated a number of different types of boron doped synthetic diamond materials which fulfill these functional electrochemical properties. The materials may be categorized into three main types:
 bulk boron doped single crystal synthetic diamond materials which comprise a suitable boron dopant content and crystallographic quality to achieve the previously described functional electrochemical properties throughout a majority volume of the single crystal synthetic diamond materials;
 capped boron doped single crystal synthetic diamond materials which comprise a capping layer having a suitable boron dopant content and crystallographic quality to achieve the previously described functional electrochemical properties and a support layer having a lower boron content; and
 boron doped polycrystalline synthetic diamond materials which comprise a plurality of boron doped synthetic diamond grains with a sufficient portion of the grains at an exposed surface of the material having a suitable boron dopant content, while maintaining phase purity (i.e. substantially no sp2 carbon content), to achieve the previously described functional electrochemical properties.

Each of these material types have their own pros and cons as summarized below.

The best material from a functional perspective is believed to be bulk boron doped single crystal synthetic diamond materials as these can, at least in principle, provide the most uniform material characteristics and thus the most uniform functional electrochemical properties. However, such materials are inherently expensive and difficult to manufacture and it is inherently difficult to grow a thick, free-standing plate of single crystal synthetic diamond material with the correct compositional requirements to fulfill the desired functional electrochemical properties at reasonable growth rates. For example, the high boron concentrations required lead to a reduction in growth rate and thus an increase in cost. Furthermore, growth parameters must be carefully controlled to prevent substantial crystallographic defects forming when growing thick layers of such material at very high boron doping concentrations. That said, the present inventors have achieved synthesis of such material and thus the limiting factor in the application of such material is likely to be cost.

Capped boron doped single crystal synthetic diamond materials are easier and cheaper to fabricate as only a relatively thin layer of highly boron doped material is required to be grown to achieve the previously described functional electrochemical properties on a thicker supporting layer that can be made with a lower boron concentration which is sufficient to achieving electrical connection to the capping layer but which in itself would not provide the previously described functional electrochemical properties. One problem with such capped materials is that the capping layer can delaminate from the support layer in use making the material less robust than a bulk boron doped single crystal synthetic diamond material. Furthermore, the use of a supporting layer having lower boron content, and thus higher electrical resistivity, will increase the power consumption of the device in use.

Boron doped polycrystalline synthetic diamond materials are the most easy and cheap to fabricate, especially when larger area electrodes are required or where large area wafers are fabricated and processed to produce a large number of smaller electrodes in a single growth run. However, boron content varies between individual grains in a boron doped polycrystalline synthetic diamond materials which will inherently lead to a less uniform material with less uniform functional electrochemical properties. That said, it has been found that if at least a portion of the grains at an exposed surface of the material have a suitable composition then the previously described functional electrochemical properties can be achieved if sp2 carbon content is reduced or eliminated. As such, by suitable optimization this material has been made sufficiently good from an electrochemical performance perspective to be adequate for many electrochemical sensing applications.

In addition to the above, another type of boron doped diamond material which is considered to be advantageous for electrochemical applications is one in which alternating layers of boron-doped and non-boron-doped material are provided. These layered structures may be fabricated by periodically introducing boron into the growth process to build up a layered structure. Vertically slicing such material can then reveal a surface which comprises alternating bands of boron-doped and non-boron-doped material to form a band sensor structure. Such a structure can be fabricated in polycrystalline or single crystal synthetic diamond material.

Whichever of the aforementioned types of material is provided, it has been found to be advantageous to fabricate a boron doped synthetic diamond material in which at least a portion of an exposed surface layer comprises boron doped synthetic diamond material having a boron content in a range $1\times10^{20}$ boron atoms cm$^{-3}$ to $7\times10^{21}$ boron atoms cm$^{-3}$. Preferably at least 50%, 70%, 90%, or 95% of the exposed surface layer comprises boron doped synthetic diamond material having a boron content in a range $1\times10^{20}$ boron atoms cm$^{-3}$ to $7\times10^{21}$ boron atoms cm$^{-3}$.

It has been found that boron doped synthetic diamond material can be fabricated with a boron content over $1\times10^{22}$ boron atoms $cm^{-3}$. However, while such material can provide a low $\Delta E_p$ it possesses a relatively high capacitance (e.g. greater than 10 μF $cm^{-2}$). Furthermore, as the boron content is increased the sp2 carbon content and crystallographic defects tend to increase which also detrimentally increases the capacitance of the material in addition to lowering the solvent window. Accordingly, the present inventors have found that a suitable upper limit for boron concentration is $7\times10^{21}$ boron atoms $cm^{-3}$ when taking all these factors into account.

Conversely, if the boron content is lowered below $1\times10^{20}$ boron atoms $cm^{-3}$ the material is found to have a large solvent window (up to 8 V if the boron content is sufficiently low that the material exhibits p-type semi-conductive behavior) and a low capacitance with a flat electrochemical response. However, such material possesses a large $\Delta E_p$ (over 70 mV and even up to several hundred mV). As such, it has been found to be advantageous to select a boron content falling within the range $1\times10^{20}$ boron atoms $cm^{-3}$ to $7\times10^{21}$ boron atoms $cm^{-3}$. For example, at least a portion of an exposed surface layer may comprise boron doped synthetic diamond material having a boron content of at least $2\times10^{20}$ boron atoms $cm^{-3}$, $3\times10^{20}$ boron atoms $cm^{-3}$, $5\times10^{20}$ boron atoms $cm^{-3}$, $7\times10^{20}$ boron atoms $cm^{-3}$, $9\times10^{20}$ boron atoms $cm^3$, $1\times10^{21}$ boron atoms $cm^{-3}$, or $3\times10^{21}$ boron atoms $cm^{-3}$. Furthermore, said portion of the exposed surface layer may comprise boron doped synthetic diamond material having a boron content of no more than $6\times10^{21}$ boron atoms $cm^3$, $5\times10^{21}$ boron atoms $cm^{-3}$, $4\times10^{21}$ boron atoms $cm^3$, $3\times10^{21}$ boron atoms $cm^{-3}$, $2\times10^{21}$ boron atoms $cm^{-3}$, or $1\times10^{21}$ boron atoms $cm^{-3}$. Exemplifying ranges include $2\times10^{20}$ boron atoms $cm^{-3}$ to $5\times10^{21}$ boron atoms $cm^{-3}$, $4\times10^{20}$ boron atoms $cm^{-3}$ to $3\times10^{21}$ boron atoms $cm^{-3}$, or $8\times10^{20}$ boron atoms $cm^{-3}$ to $1\times10^{21}$ boron atoms $cm^{-3}$. For certain embodiments a boron content in a range $1\times10^{20}$ boron atoms $cm^{-3}$ to $1\times10^{21}$, $1\times10^{20}$ boron atoms $cm^{-3}$ to $7\times10^{20}$ boron atoms $cm^{-3}$, or $1.5\times10^{20}$ boron atoms $cm^{-3}$ to $5\times10^{20}$ boron atoms $cm^{-3}$ may be preferable.

Boron content can be measured by secondary ion mass spectrometry (SIMS). The boron concentration value obtained using SIMS can be variable according to how the SIMS measurements are performed and calibrated. The aforementioned values correspond to those obtained using a calibrated SIMS measurement technique as outlined below.

SIMS is calibrated by assuming the proportion of the boron signal is a linear function of the carbon signal in the diamond over the concentration range $1\times10^{14}$ atoms $cm^{-3}$ to $7\times10^{21}$ atoms $cm^{-3}$. A calibration standard was prepared by ion implantation of boron into a single crystal diamond sample with a peak boron concentration of $1\times10^{19}$ atoms $cm^{-2}$ at a depth of 1 μm. A SIMS profile versus sample depth is used to generate the linear calibration factor for the given experimental conditions. All samples in this study have been calibrated against a single standard.

As an alternative to the above, is possible to measure the boron concentration from a suitably calibrated Raman spectrometry technique. Even if a Raman spectrometry technique is not calibrated, qualitative information regarding the boron content of the material can be discerned. For example, the boron concentration can be qualitatively investigated by evaluating the area of the Raman peak at approximately 1332 $cm^{-1}$ and the asymmetry of this peak. Fano resonance causes an asymmetry in this peak and indicates a boron concentration of greater than $1\times10^{20}$ boron atoms $cm^{-3}$. A peak from boron-boron interactions is also seen for high boron concentrations from 550 to 400 $cm^{-1}$. This peak shifts to lower wavenumbers and becomes more intense with increasing boron concentration. Micro-Raman spectroscopy can be used to map the boron concentration in this manner for individual grains in a polycrystalline synthetic diamond material.

As previously described, one embodiment of the present invention comprises a single crystal synthetic diamond material which is bulk boron doped such that all, or substantially all, of the single crystal synthetic diamond material is doped to a level suitable to achieve the previously described electrochemical properties. For example, the single crystal synthetic diamond material may comprise a boron dopant concentration as defined above throughout a majority volume of at least 50%, 60%, 70%, 80%, 90%, or 95% of the single crystal synthetic diamond material. However, it is noted that the functional performance of the material in electrochemical applications will be dependent on the concentration of boron at an exposed working surface and so the single crystal synthetic diamond material should preferably at least comprise a boron dopant concentration as defined above over at least majority of the exposed working surface of the material (e.g. at least 50%, 60%, 70%, 80%, 90%, or 95% of exposed working surface).

Alternatively, the single crystal boron doped synthetic diamond material may comprise one or more layers having a boron content as previously defined. For example, the material may comprise alternating layers of boron-doped and non-boron-doped material forming a band electrode structure. Alternatively, the material may comprise a highly doped capping layer and a support layer having a lower boron content than the capping layer. In this case, the support layer may have a boron content of at least $5\times10^{18}$ boron atoms $cm^{-3}$, $1\times10^{19}$ boron atoms $cm^{-3}$, $5\times10^{19}$ boron atoms $cm^{-3}$, $1\times10^{20}$ boron atoms $cm^{-3}$, or $3\times10^{20}$ boron atoms $cm^{-3}$. Such a level of boron dopant can provide sufficient electrical conductance to electrically address the capping layer. The capping layer may have a range 1 nm to 100 μm, 5 nm to 50 μm, 10 nm to 20 μm. Such thin capping layers are easier to fabricate with very high boron concentrations when compared to thicker layers. Furthermore, thin capping layers can be made with a more uniform distribution of boron dopant when compared with thicker layers of material. Optionally, the support layer may be grown first and then a growth surface thereof may be processed to reduce the roughness of the growth surface prior to growing a capping layer thereon.

Alternatively still, the boron doped synthetic diamond material may be provided by a polycrystalline boron doped synthetic diamond material. Such material generally contains grains of diamond material with varying concentrations of boron dopant. In accordance with certain polycrystalline boron doped synthetic diamond materials only a portion of the grains at an exposed working surface of the electrode material may have a boron content within the defined ranges. For example, at least 1%, 5%, 10%, 20%, 30%, 50%, 70%, 90%, 95%, or substantially all of the grains in an exposed surface layer may have a boron content as previously defined.

Boron uptake in polycrystalline synthetic diamond material varies between grains as the grains can be oriented in different crystallographic orientations during growth and different crystallographic orientations have a differential rate of boron uptake. Due to differential boron uptake in the grains of the polycrystalline synthetic diamond material it has been found that if the proportion of grains having very high boron content is increased then a significant portion of grains may have a boron content which is too high, which can lead to an increase in the capacitance of the material. Furthermore, as the boron content is pushed too high a significant proportion of sp2 carbon can be formed in the material during growth. As such, certain polycrystalline synthetic diamond materials may comprise only a portion of grains having the desired boron content for optimized electrochemical performance. For example, no more than 70%, 60%, 50%, 40%, 35%, 30%, 25%, 20%, 15%, 10%, or 5% of grains in an exposed surface layer may have a boron content within a range $1 \times 10^{20}$ boron atoms $cm^{-3}$ to $7 \times 10^{21}$ boron atoms $cm^{-3}$ as previously defined. The remaining grains may have a lower boron content. However, it is advantageous that at least 60%, 70%, 80%, or 90% of grains in an exposed surface layer have a boron content no less than $1 \times 10^{19}$ boron atoms $cm^{-3}$ and preferably no less than $1 \times 20^{20}$ boron atoms $cm^{-3}$. A majority of the grains may thus have a boron content above $1 \times 10^{19}$ boron atoms $cm^{-3}$ with a proportion of the grains having a boron content above $1 \times 10^{20}$ boron atoms $cm^{-3}$. For example, 5% to 50%, 10% to 45%, 15% to 40%, 20% to 40%, or 25% to 35% of grains in the exposed surface layer of the material having a boron content in a range $1 \times 10^{20}$ boron atoms $cm^{-3}$ to $7 \times 10^{21}$ boron atoms $cm^{-3}$. Furthermore, 50% to 95%, 55% to 90%, 60% to 85%, 60% to 80%, or 65% to 75% of grains in an exposed surface layer may have a boron content in a range $1 \times 10^{19}$ boron atoms $cm^{-3}$ to $1 \times 20^{20}$ boron atoms $cm^{-3}$.

According to the above, certain polycrystalline synthetic diamond materials only comprise a proportion of grains at a working surface of the material which exhibit metal-like conductivity and it is difficult to control growth such that all grains at a working surface of the material exhibit metal-like conductivity without introducing a significant proportion of sp2 carbon into the material during growth. The remaining grains may exhibit hopping conduction but may even be down in the semiconductor conduction range. Of course, if boron uptake in the grains of the polycrystalline diamond material can be made more uniform, for example by growing the material such that the grains tend to grow in a selected crystallographic orientation, then it is be possible to increase the proportion of grains at a working surface which have a boron content in the desired range $1 \times 10^{20}$ boron atoms $cm^{-3}$ to $7 \times 10^{21}$ boron atoms $cm^{-3}$ without also incorporating a significant portion of sp2 carbon into the material during growth.

In fact, the present inventors have optimized the growth process of boron doped polycrystalline diamond material to achieve a working surface which comprises all, or substantially all, grains within the metal-like conductivity regime without also incorporating a significant portion of sp2 carbon into the material during growth. This has been achieved by carefully controlling a combination of growth parameters to within a narrow region of growth parameter space which has been found to be suitable for the synthesis of such material including controlling a substrate temperature in a range 1050 to 1120° C., using a synthesis atmosphere which has a relatively low concentration of carbon containing gas (e.g. in a range 1% to 3% of total gas flow), using a high power density (e.g. 5 to 6 kW over a 50 mm diameter substrate) in combination with a relatively high reactor pressure (e.g. in the range 200 to 300 Torr (i.e. 26.66 kPa to 40.00 kPa)), and using a high gas flow configuration and high total gas flow rate. For example, using such growth conditions it is possible to synthesize polycrystalline boron doped diamond material having a working surface with an average boron concentration of $3 \times 10^{20}$ boron atoms $cm^{-3}$ including low boron content grains having a boron concentration of $1.9 \times 10^{20}$ boron atoms $cm^{-3}$ and high boron content grains having a boron concentration of $4.7 \times 10^{20}$ boron atoms $cm^{-3}$. That is, all, or substantially all, grains at the working surface have a boron concentration within the desired range in the metal-like conductivity regime.

For single crystal embodiments in which uptake of boron dopant is more uniform the majority or all of a working surface of the material can exhibit metal-like conductivity. In each case, the material should not be made "too metallic" by ramping the boron content above $7 \times 10^{21}$ boron atoms $cm^{-3}$ as this leads to an increase in capacitance and a reduction in the sensitivity of the material for electrochemical sensing applications as previously described.

Without being bound by theory, the following discussion provides a theoretical explanation of how and why electrical conductivity and electrochemical functionality of boron doped diamond materials changes with boron concentration.

In lightly boron doped diamond materials (boron concentrations less than approximately $10^{18}$ $cm^{-3}$) electrical conductivity can be explained in terms of isolated acceptors capturing thermally activated electrons from the valence band, leaving behind holes which contribute to the electrical conductivity.

A simple estimate for the binding energy expected for effective-mass-like acceptors in diamond (and other semiconductors) can be calculated from the equation $$E_A = \left(\frac{m_h}{m_0}\right)\left(\frac{1}{\varepsilon_r}\right)^2 R_y$$

with $R_y$=13.6 eV (Rydberg energy), $m_h$=hole effective mass, and $\varepsilon_r \approx 5.7$ (relative permittivity). If it is assumed that $m_h$=0.7 $m_0$ (rest mass of electron) then $E_A$=0.3 eV, fortuitously close to the actual experimental boron binding energy. Since the bound-hole ground state wave function extends over only less than three lattice constants the effective-mass theory should be very unreliable and inaccurate.

The Bohr radius (nm) of the acceptor ground state is $$a_0 = \frac{4\pi\varepsilon_0\varepsilon_r\hbar^2}{m_h e^2} = 0.053\varepsilon_r \frac{m_0}{m_h}$$

Taking $\varepsilon_r$=5.7 and $m_h$=0.7 $m_0$ then $a_0$=0.43 nm.

As the concentration of boron acceptors is increased it becomes possible for hopping conduction between acceptors that have a trapped electron and those which are neutral to contribute to the overall electrical conduction. At even higher concentrations the acceptor wave-functions will begin to overlap. This will lead to delocalisation and the formation of an impurity band with the Femi level in the band leading to metallic conductivity even at zero temperature. Mott proposed that this simplified one electron picture may fail. Indeed, because of strong on-site correlations, the spin-degenerate half-filled impurity band could split into an empty and a full band. On further doping, these two bands begin to overlap and the metal-insulator transition takes place.

The metal-insulator transition (Mott transition) is expected for dopant concentrations of $$n_B > \left(\frac{0.26}{a_0}\right)^3$$

where $n_B$ is the boron dopant density of the material. With $a_0$=0.43 nm we estimate $n_b$>6×10$^{20}$ cm$^{-3}$. If the criterion is satisfied the material becomes conductive (metal) and otherwise it will be an insulator (Kittel, Charles (2005), *Introduction to Solid State Physics* (8th ed.), John Wiley & Sons, p. 407-409).

The value of $n_b$>6×10$^{20}$ cm$^{-3}$ for the Mott transition should be treated cautiously given the gross simplifications made in its calculation and note in the simple calculations we would have a higher value ($n_b$>6×10$^{20}$ cm$^{-3}$) if we had assumed that $m_h$=$m_0$. A value of $n_b$>4×10$^{20}$ cm$^{-3}$ has been reported (T. Klein et al, Metal insulator transition and superconductivity in boron-doped diamond, 2007, Physical Review B. Condensed Matter and Materials Physics, (75), 165313. http://dx.doi.org/10.1103/PhysRevB.75.165313). However, given the available experimental and theoretical data it is reasonable to assume that the metal insulator transition for boron doped diamond occurs in the range $n_b$>1-5×10$^{20}$ cm$^{-3}$.

Figure 6:
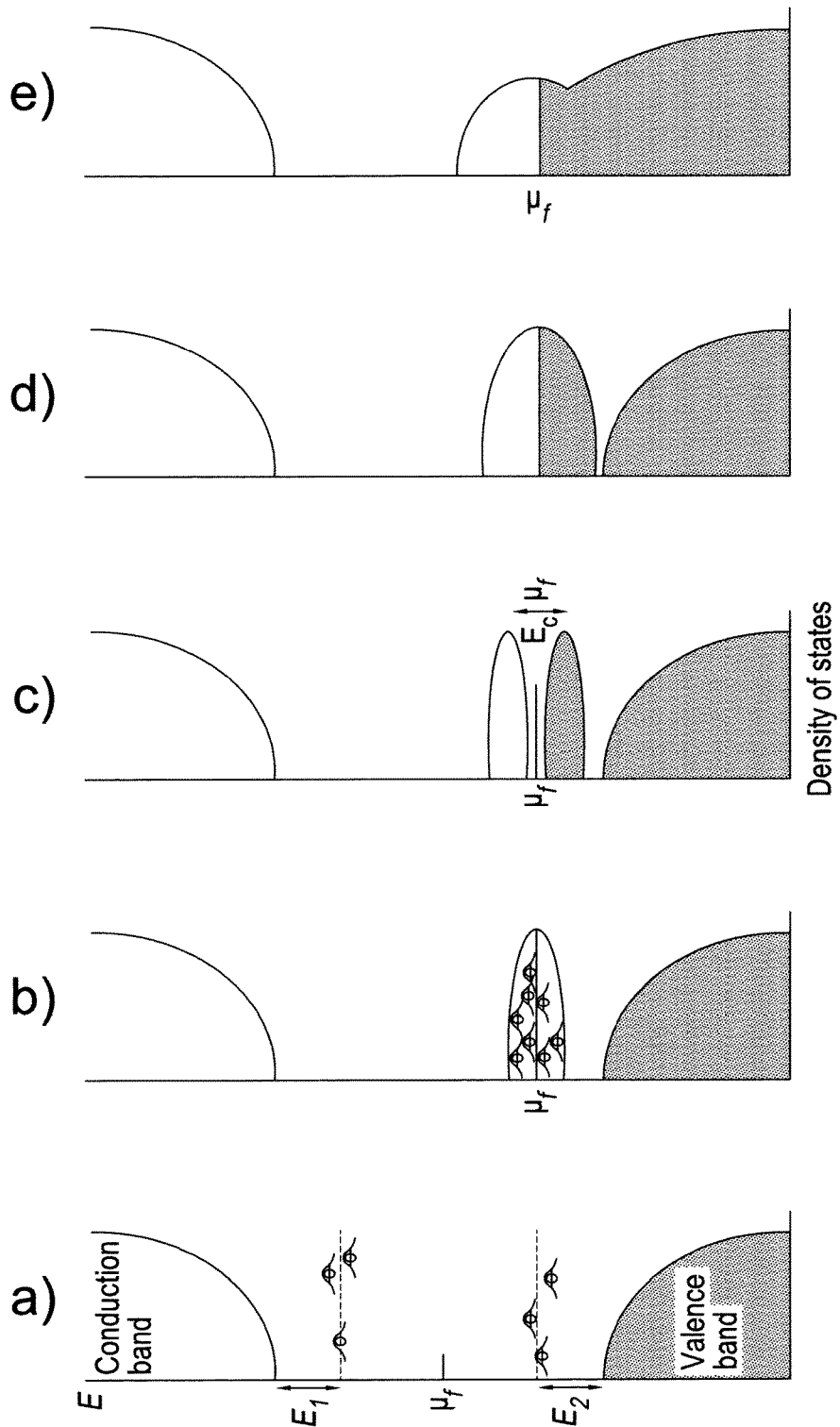
FIGS. 6(a) to (e) show the electronic density of states and band structure of boron doped diamond material with increasing concentration of boron dopant illustrating different electrical conduction regimes for boron doped synthetic diamond materials including semiconductive behavior, hopping conduction, and metallic conduction.

FIG. 6 (Blase et al, Progress Article. Nature Materials 8, 375-382, 2009) shows the evolution of the electronic density of states and band structure with increasing p-type doping. The doping increases from (a) to (e). The shaded areas represent filled states and $\mu_F$ the Fermi Energy.

For diamond doped with boron at concentrations $n_b$>1-5×10$^{20}$ cm$^{-3}$ metal-like electrical conductivity would be expected. However, it would not be expected that the density of states is sufficiently high for a good metal. Nevertheless, the density of states should be sufficient to support the currents in electro-analytical applications of diamond. As well as sufficiently high boron doping to ensure metallic like conductivity it is also required that the attractive electrochemical properties of diamond (e.g. corrosion resistance, low background currents, wide potential window, etc. . . . ) are not degraded. This could happen, for example, if with increasing boron doping there is a simultaneous increase in the incorporation of non-diamond material (e.g. sp2 carbon). In this work it has been found that for boron concentrations in excess of 7×10$^{21}$ boron atoms cm$^{-3}$ it is increasingly difficult to suppress unwanted material phases. As such, it has been found to be advantageous to select a boron content falling within the range 1×10$^{20}$ boron atoms cm$^{-3}$ to 7×10$^{21}$ boron atoms cm$^{-3}$. For example, within a range 2×10$^{20}$ boron atoms cm$^{-3}$ to 5×10$^{21}$ boron atoms cm$^{-3}$, 4×10$^{20}$ boron atoms cm$^{-3}$ to 3×10$^{21}$ boron atoms cm$^{-3}$, or 8×10$^{20}$ boron atoms cm$^3$ to 1×10$^{21}$ boron atoms cm$^{-3}$.

As alluded to above, in addition to controlling boron dopant content, in order to achieve material having optimized electrochemical characteristics it has been found to be important to minimize the formation of sp2 carbon during growth of the boron doped synthetic diamond material. Raman spectroscopy has been found to be a particularly useful technique for measuring sp2 carbon content. Non-diamond carbon peaks include: 1580 cm$^{-1}$—graphite; 1350-1580 cm$^{-1}$—nanocrysallite graphite; and 1550-1500 cm$^{-1}$—amorphous carbon and graphitic phases. It has been found that if sp2 carbon is evident in a Raman spectrum of a material then the material will have a smaller solvent window, a higher capacitance, and surface oxidation/reduction features. Accordingly, preferably the sp2 carbon content is sufficiently low as to not exhibit non-diamond carbon peaks in a Raman spectrum of the material. An sp2 carbon signature in Raman spectra has been correlated with higher capacitance, non-Faradaic surface processes, and a reduced solvent window. Micro-Raman spectroscopy can be performed at room temperature with a Renishaw inVia Raman microscope using an excitation wavelength of 514.5 nm, an Ar$^+$ laser with a power of 10 mW, and a CCD detector. Magnification for Raman spectroscopy can be ×5, ×10, ×20, ×50 and ×100 objectives at visible and near infrared (NIR) frequencies and ×5 and ×20 at ultraviolet (UV) frequencies. With ×50 magnification the xy-spot size (and hence resolution) is approximately 5×5 microns and with ×100 the xy-spot size is approximately 2×2 microns. Typical values for magnification objectives in air thus range from ×5 to ×100.

In addition to the boron and sp2 carbon compositional requirements discussed above, it has also been found to be desirable to fabricate material which comprises little or no crystallographic defects observable by DIC (Normaski) visible microscopy at a magnification of up to ×100. For example, samples of boron doped single crystal synthetic diamond material have been found to exhibit small rod-like features, extended polycrystalline inclusions, which are visible using microscope imaging. Such defects can result in variable electrochemical behavior and are thus considered undesirable. As such, it is considered desirable to minimize such defects either by controlled growth or by processing material by selecting areas of material which are substantially free of such defects to form electrochemical electrodes. As such, advantageously an exposed surface of the single crystal boron doped synthetic diamond material may comprise no more than 5%, 3%, 1%, 0.5%, or 0.3% by area of crystallographic defects observable by visible microscopy at a magnification of up to ×100.

In addition to compositional requirements of the material in terms of impurities, dopants, and crystallographic quality, the surface characteristics of the material can also affect functional performance in electrochemical applications. For example, it has been found that if the surface of the material is too rough then the capacitance increases beyond that which is desirable. Accordingly, an exposed working surface of the material should advantageously be processed to a surface roughness such that capacitance is not adversely affected. For example, to a surface roughness $R_a$ of no more than 20 nm or most preferably no more than 10 nm. Furthermore, the boron doped synthetic diamond material may be processed to have a thickness variation of no more than ±0.05 mm.

Furthermore, it is also advantageous to minimize surface and sub-surface damage at an exposed working surface. This may be in the form of microcracks and chips formed by surface processing or otherwise inherent to the as-grown material. Such surface and sub-surface damage features can be quantified using a revealing plasma etch as described, for example, in EP1292726. As such, preferably an exposed working surface of the boron doped diamond material, particularly for single crystal embodiments, has a density of surface defect features, as revealed by a revealing plasma etch, below 5×10$^3$/mm$^2$ and more preferably below 10$^2$/mm$^2$. After lapping and polishing the exposed working surface, the exposed working surface can be subjected to a plasma etch to minimise surface damage of the surface as described in EP1292726. Alternatively, if the growth process is controlled to fabricate a low surface roughness diamond material then it can be possible to use as-grown diamond material without requiring post-growth processing which can impart damage into the surface of the material. For polycrystalline diamond materials which will tend to have a growth surface with a relatively high roughness, post-growth lapping and polishing should be controlled to ensure that the processed surface has a low level of surface and sub-surface damage.

Furthermore, the type of surface termination on the surface of the synthetic diamond material can also affect functional performance in electrochemical applications. For example, for low boron content synthetic diamond material (e.g. with a boron content of less than $1\times10^{19}$ atoms $cm^{-3}$) $\Delta E_p$ can be advantageously reduced by treating the material so as to provide a hydrogen termination. As such, this may seem advantageous. However, such a hydrogen terminated surface is inherently unstable when subjected to applied electrochemical potentials, and thus will gradually deteriorate in performance over time as the hydrogen termination is lost resulting in a large increase in $\Delta E_p$. In contrast, the materials described herein are able to achieve the defined electrochemical functional parameters even with an oxygen terminated surface. Further still, it has been found that the materials described herein have electrochemical functional parameters which are very stable to changes in surface termination. This allows stable device performance which is highly advantageous for a commercially viable product. For example, the materials described herein can exhibit a $\Delta E_p$ which changed by no more than 5 mV, 4 mV, 3 mV, 2 mV, or 1 mV by changing surface termination of an exposed surface of the boron doped synthetic diamond material from oxygen terminated to hydrogen terminated. In this work, all electrochemical measurements were performed with oxygen-terminated synthetic diamond materials. Such surfaces can be typically achieved by acid washing (boiling diamond in concentrated 12M $H_2SO_4$ saturated with $KNO_3$ for 30 minutes) and then polishing the surface of the synthetic diamond material with alumina micro polish (0.05 μm) for 2 minutes prior to placing the material in solution for analysis.

As discussed above, for boron doped diamond materials according to the present invention, surface termination has been found to have little impact on electron transfer kinetics and electrochemical performance. However, it should be noted that this is in relation to "outer-sphere" reactions. An outer-sphere reaction is one in which the reactants, products, and intermediates do not interact strongly with the electrode material and electron transfer occurs by tunneling across at least a monolayer of solvent. In contrast, an "inner-sphere" reaction is one in which there is a strong interaction of reactant or product with the electrode surface. For inner-sphere reactions, the reactants, intermediates, or products are often specifically adsorbed on the electrode surface. These inner-sphere reactions will be affected by the surface termination of the boron doped diamond material. Furthermore, it has been found that the functional groups which reside on the boron doped synthetic diamond surface are dependent on crystal orientation of the boron doped diamond material as well as the method of surface termination. In this regard it has been found that a {100} oriented boron doped diamond surface has better electrochemical performance than other crystallographic orientations such as {110} and {111} oriented materials for inner-sphere reactions. As such, the boron doped synthetic diamond material of the present invention may preferably comprise a working surface which lies within 20°, 10°, 5°, 4°, 3°, 2°, or 1° of a {100} crystallographic plane. For single crystal materials substantially all the working surface may be formed in this crystallographic orientation (at least 50%, 60%, 70%, 80%, or 90% of a working surface of the boron doped synthetic diamond material). For polycrystalline boron doped diamond material it is usual that a combination of {100}, {111}, and {110} surfaces will be exposed. As such, it is considered that correctly oriented single crystal diamond materials will be superior for certain inner-sphere reactions. Such a crystallographic orientation may be used in combination with oxygen termination.

In addition to the above, for many applications it is also advantageous for the boron doped synthetic diamond material to be mechanically robust and have good thermal conductivity. For example, the boron doped synthetic diamond material may have one or more of the following characteristics:

a nucleation side fracture stress of no less than 760 MPa, more preferably no less than 800 MPa;

a growth side fracture stress of no less than 400 MPa, more preferably no less than 450 MPa;

a Young's modulus no less than 950 MPa, more preferably no less than 1000 MPa;

a fracture toughness no less than 7 MPa $m^{1/2}$, more preferably no less than 8 MPa $m^{1/2}$;

a Weibull modulus no less than 9, more preferably no less than 10;

a hardness no less than 70 GPa, more preferably no less than 80 GPa; and a thermal conductivity no less than 600 W/mK, more preferably no less than 700 W/mK as measured through plane at 300 K.

In addition to the boron doped synthetic diamond material characteristics as described above, it is also important to ensure that a good ohmic contact is provided to the boron doped synthetic diamond material for sensing applications. In this regard, the contact resistance of the ohmic contact may be the same order of magnitude or less than the resistivity of the boron doped synthetic diamond material. For example, the contact resistance may be less than $1\times10^{-3}$ Ohm m and the resistivity of the boron doped synthetic diamond material may also be less than $1\times10^{-3}$ Ohm m. An ohmic contact may be provided by graphitizing a surface portion of the boron doped synthetic diamond material and bonding to the graphitized surface portion with a metal bond such as gold. Alternatively, a carbide forming metal may be deposited on a surface portion of the boron doped synthetic diamond material to form a thin metal carbide layer on which a bonding metal can be deposited. For example, titanium may be deposited to form a thin titanium carbide layer and a metal such as gold can be deposited on the titanium carbide layer to form a metal bond for the ohmic contact. One useful ohmic contact comprises a layered structure comprising titanium, platinum, and gold layers. The titanium layer provides a carbide layer on a surface portion of the boron doped synthetic diamond material to which metal layers can be bonded. The platinum layer provided an intermediate passivation barrier to prevent any adverse reaction between overlying bonding metals, such as gold, and an underlying carbide layer, such as titanium carbide.

Experimental work supporting the above-described invention is set out below. The experimental work is described in four sections. A first section relates to diamond synthesis. A second section relates to polycrystalline boron doped diamond (pBDD) materials and includes a comparison of a pBDD material in accordance with the present invention with several pBDD materials not according to the present invention. A third section relates to single crystal boron doped diamond (scBDD) materials including both bulk boron doped single crystal diamond materials and single crystal diamond materials including a capping layer of highly doped material. Finally, a fourth section illustrates an exemplifying use of these materials as a hydrogen sulphide sensor.

Synthesis of Boron Doped Diamond Materials

Materials according to embodiments of the present invention have been fabricated using a microwave plasma activated chemical vapour deposition (CVD) synthesis process. A microwave plasma activated CVD diamond synthesis system typically comprises a plasma reactor vessel coupled both to a supply of source gases and to a microwave power source. The plasma reactor vessel is configured to form a resonance cavity supporting a standing microwave, typical frequencies used for this heating application include 2.45 GHz and approximately 900 MHz depending on the RF spectrum allocation of each country. In this work the example conditions are given for a system equipped with a 2.45 GHz microwave source. Source gases including a carbon source and molecular hydrogen are fed into the plasma reactor vessel and can be activated by the standing microwave to form a plasma in high field regions. If a suitable substrate is provided in close proximity to the plasma, reactive carbon containing radicals can diffuse from the plasma to the substrate and be deposited thereon. Atomic hydrogen can also diffuse from the plasma to the substrate and selectively etch off non-diamond carbon from the substrate such that diamond growth can occur. If a source of boron such as diborane gas is introduced into the synthesis atmosphere then boron doped synthetic diamond material can be grown. Single crystal synthetic diamond materials are typically fabricated via homoepitaxial growth on single crystal diamond substrates. In contrast, polycrystalline synthetic diamond wafers can be grown on silicon or refractory metal substrates.

Important growth parameters include the microwave power density introduced into the plasma chamber (typically ranging from less than or equal to 1 kW to 5 kW or more for a substrate area <20 cm$^2$), the pressure within the plasma chamber (typically ranging from less than or equal to 50 Torr (i.e. 6.67 kPa) to 350 Torr (i.e. 46.66 kPa) or more), the gas flow velocity flowing through the plasma chamber (typically ranging from a few 10s of sccm (standard cm$^3$ per minute) up to hundreds or even thousands of sccm), the temperature of the substrate (typically ranging from 700 to 1200° C.), and the composition of the synthesis atmosphere (typically comprising 1 to 20% by volume of carbon containing gas (usually methane) with the remainder of the synthesis atmosphere been made up of hydrogen). For boron doping the synthesis atmosphere will typically comprise a boron containing gas such as diborane at a concentration from equal to or less than 0.01% up to several % by volume.

The problem to be solved is what growth parameters to select in order to fabricate synthetic boron doped diamond materials with optimized electrochemical sensing properties. Suitable growth parameters for both single crystal and polycrystalline diamond materials are discussed below.

Single Crystal Boron Doped Diamond Materials

As previously described, a boron dopant concentration in a range $1\times10^{20}$ boron atoms cm$^{-3}$ to $7\times10^{21}$ boron atoms cm$^{-3}$ has been found to be desirable to achieve high performance synthetic diamond material for electrochemical sensing applications. However, it has also been found that electrochemical performance of single crystal boron doped diamond materials can be affected by the presence of crystallographic defect features which are observable by visible microscopy at a magnification of up to ×100. It has been found that growing single crystal CVD synthetic diamond material at higher power and pressure (e.g. 250 Torr (i.e. 33.33 kPa); 5.0 kW at an operating frequency of 2.45 GHz with a 5 cm diameter carrier substrate area) produces better crystal quality material but at high powers and pressures the uptake of boron dopant is reduced such that the required levels cannot be achieved. Conversely, if the power and pressure are reduced (e.g. 100 Torr (i.e. 13.33 kPa); 2 kW) then boron uptake is increased to the desired level but the crystal quality of the material is reduced such that the desired electrochemical parameters are not achieved. It has been found that there is a narrow operating window within which the power and pressure are sufficiently high to achieve the required crystal quality and sufficiently low to achieve the desired level of boron dopant uptake. Preferably the pressure is controlled to lie in a range 120 Torr to 160 Torr (i.e. 16.00 kPa to 21.33 kPa), more preferably in a range 130 Torr to 150 Torr (i.e. 17.33 kPa to 20.00 kPa), and most preferably around 140 Torr (i.e. 18.67 kPa). In addition, preferably the power is controlled to lie in a range 3.1 kW to 3.9 kW, more preferably in a range 3.3 kW to 3.8 kW, and most preferably around 3.6 kW. The temperature of the substrate may be controlled to lie in a range 750° C. to 850° C.

In addition to the above, boron incorporation has been found to be increased by manipulating the gas flow firstly by using a reactor configured with a co-axial gas injection system, for example comprising a nozzle positioned between 50 mm and 180 mm above the substrate to direct gas towards the substrate, and secondly by increasing the gas velocity via a combination of the total gas flow rate and the chamber gas injection nozzle diameter. Using an axial gas injection nozzle with a diameter of 2 mm, positioned 75 mm above the substrate, the total gas flow rate may be at least 500 sccm, more preferably at least 600 sccm, and most preferably over 650 sccm. For example, a hydrogen gas flow of between 500 and 700 sccm may be utilized with a methane gas flow of between 25 and 40 sccm and a diborane gas flow between 15 and 30 sccm. Argon gas may also be introduced into the synthesis atmosphere, for example at a flow rate in a range 20 to 30 sccm. Only by providing these growth parameters in combination has it been found to be possible to achieve single crystal diamond growth which meets both the boron content and crystallographic quality requirements which result in a material having the electrochemical performance characteristics as described herein. It has also been found that providing a shallow miss-cut angle on the single crystal diamond substrates relative to a crystallographic plane can aid in promoting step-flow growth leading to higher crystallographic quality material for a given power and pressure.

Polycrystalline Boron Doped Diamond Materials

Similar comments as those set out above for single crystal boron doped diamond also apply for polycrystalline boron doped diamond material. Having regard to polycrystalline material, the problem is how to achieve the high levels of boron doping while avoiding incorporation of sp2 carbon during growth. This has been achieved by controlling substrate temperature in a range 1050 to 1120° C., using a synthesis atmosphere which has a relatively low concentration of carbon containing gas (e.g. in a range 1% to 3% of total gas flow), a high power density (e.g. 5 to 6 kW over a 50 mm diameter substrate) in combination with a relatively high reactor pressure (e.g. in the range 200 to 300 Torr (i.e. 26.66 kPa to 40.00 kPa)) using a high gas flow configuration and total flow rate as previously described for single crystal growth.

Polycrystalline Boron Doped Diamond (pBDD) Materials

Several fast electron transfer outer-sphere redox species have been used to investigate the effect of density of states via boron doping on the electron transfer properties for oxygen-terminated synthetic diamond samples of varying levels of boron dopant (five polycrystalline boron doped synthetic diamond samples A to E are discussed herein, samples A to D being comparative examples and sample E being an embodiment of the present invention). This effect is considered in light of the formal redox potential and rearrangement kinetics of the systems being probed. It is also shown how the boron content and non-diamond carbon content observed in micro-Raman are reflected in the potential windows and background currents for boron doped synthetic diamond electrodes. It is also shown that synthetic diamond material with a significant sp2 carbon content can produce narrower potential windows, background redox processes, and larger capacitance values.

Diamond Characterisation

The effect of boron concentration and diamond quality on electrochemistry was investigated using five pBDD samples A to E of varying boron and sp2 carbon content. All were grown via microwave chemical vapour deposition, sample A from the Naval Research Laboratory, whereas samples B, D and E were grown by Element Six Ltd and sample C was grown by Advanced Diamond Technologies Inc. Prior to electrochemistry, the material properties were characterised using secondary ion mass spectrometry (SIMS), resistivity measurements, field-emission scanning electron microscopy (FE-SEM) and micro-Raman. The average boron content for the samples was determined by SIMS and was found increase from below $2\times10^{18}$ atoms $cm^{-3}$ up to $7\times10^{20}$ atoms $cm^{-3}$ for the sample sequence A to E (for example, $2\times10^{18}$ atoms $cm^{-3}$ for sample B, $3\times10^{20}$ atoms $cm^{-3}$ for sample D, and $7\times10^{20}$ atoms $cm^{-3}$ for samples E). Resistivity values of $4.07\times10^{4}$, 87.9, 0.1, 0.085 and 0.039 $\Omega cm$ for samples A to E respectively confirmed that the resistivity decreases with an increasing average boron concentration. These values coincide with those determined by Lagrange et al. in which single crystal BDD of varying boron concentrations were studied. From the resistivity measurements it is expected that samples A and B conduct via the valence band and thus behave as semi-conductors, whereas the resistivity of sample C suggests a hopping conduction mechanism. The more highly doped samples D and E lie just within the metallic conduction regime, where differing grains within the polycrystalline samples could exhibit either hopping or metallic conduction.

Figure 7:
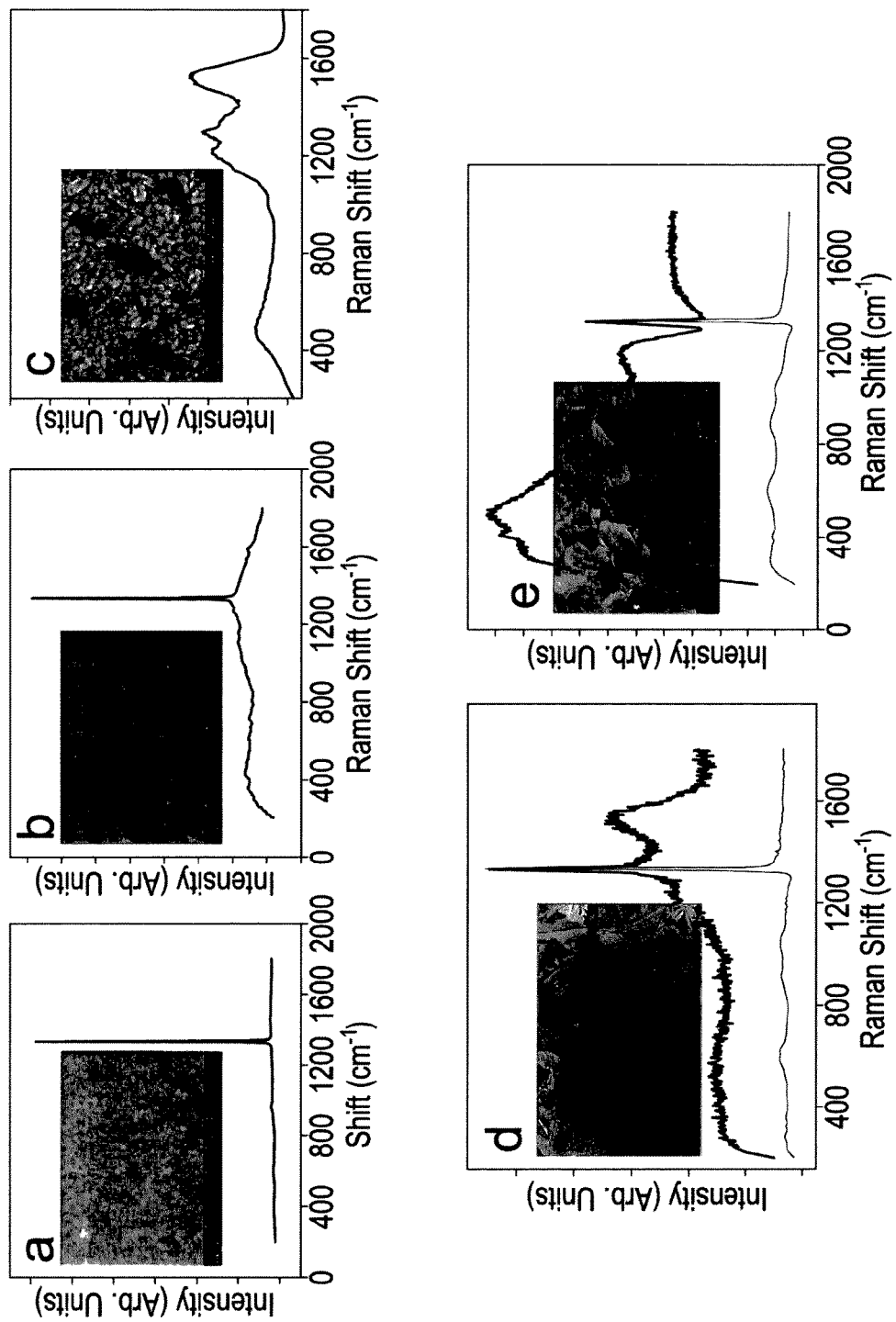
FIG. 7 illustrates field emission scanning electron micrographs and Raman spectra for five polycrystalline boron doped diamond samples A to E, sample E being an embodiment of the present invention.

FE-SEM was carried out to assess the grain morphology of the diamond surfaces. The inserts in FIG. 7 show the in-lens secondary electron FE-SEM images of: (a) sample A; (b) sample B; (c) sample C; (d) sample D; and (e) sample E. Samples A, B, D and E show low surface roughness due to the polishing process in which the pBDD is rotated and translated while in contact with a spinning polishing wheel. The resulting features are individual grains of different growth facets, where the contrast is due to grain-dependant boron uptake i.e. boron is more readily incorporated, by a factor of approximately 10, into (111) growth sectors than (100) sectors. On the other hand, sample C is a 2 µm thin film grown on a $SiO_2$ wafer and was therefore too thin to polish. The FE-SEM image for sample C thus shows the deposited crystallites with a higher surface roughness. The crystallite/grain sizes reflect the relative thicknesses of the samples, where sample C has an average crystallite size of 70 nm. Of the polished samples, sample A is the thinnest and has the smallest grain size at 300 nm diameter and sample B is the thickest with grain sizes from 7 to 100 µm.

While the sample thickness of samples D and E are similar at approximately 800 µm, the randomly orientated grain structure is clearly different, most likely due to different parameters used during CVD growth. The dark regions in the FE-SEM images correlated with the more highly boron doped regions, as confirmed by cathodo-luminescence, Raman microscopy, and C-AFM maps recorded in the same area.

Micro-Raman spectroscopy was used to verify the quality of the pBDD produced, via observation of the D ($sp^3$) and G ($sp^2$) peaks in the resulting spectrum as well as to investigate the boron uptake. All samples were treated identically prior to Raman mapping by stringent acid cleaning. FIG. 7 shows typical micro-Raman spectra taken at a wavelength of 514.5 nm for: (a) sample A; (b) sample B; (c) sample C; (d) sample D; and (e) sample E. Figures (d) and (e) show two spectra where it was possible to probe the brighter and darker grains individually (the spectra corresponding to lighter grains having a lower boron content is the lower of the two spectra illustrated in Figures (d) and (e)). The diamond zone centre optical phonon peak at approximately 1332 $cm^{-1}$ is immediately obvious in all spectra apart from sample C, which may be a consequence of the nanocrystalline nature of the diamond surface. Both D peaks for samples A and B occur at 1332 $cm^{-1}$, whereas a shift to lower wavenumbers is observed for samples D and E, especially in the darker grains. A slight asymmetric deformation of the D peak can be seen for the lighter grains in FIG. 7(d) and to a greater extent in FIG. 7(e). This feature is attributed to a Fano-type interference between the discrete zone centre phonon and a continuum of electronic excitations, indicating that the grain has a dopant density in a range $1\times10^{19}$ to $1\times10^{20}$ atoms $cm^{-3}$. The Raman spectra taken at darker grains, show greatly attenuated and broadened diamond peaks, demonstrating a larger Fano effect. Samples A and B show no such attenuation verifying the above statement that these samples are not metallically doped.

Peaks at approximately 1220 $cm^{-1}$ and 500 $cm^{-1}$ have previously been recorded for boron doped diamond and were found to correlate with boron concentrations in heavily doped samples. Again, these are absent from samples A and B, but can be seen for samples C, D and E. Peaks of weak intensity can be observed in the bright grains for samples D and E at 1220 $cm^{-1}$ and 600 $cm^{-1}$ indicating a doping level just below $3\times10^{20}$ atoms $cm^{-3}$. However, a shift of the latter peak to 460 $cm^{-1}$ for the darker grains and sample C indicates a higher boron concentration. These spectra coincide with the FE-SEM showing that the darker grains have a higher boron concentration than the brighter grains. Importantly the presence of the Fano interference in both light and dark regions of the pBDD samples D and E indicate that even in the lighter doped regions, the boron concentration is $\geq1\times10^{20}$ atoms $cm^{-3}$ indicating that the regions are expected to conduct either via hopping or metal conduction.

Features due to non-diamond carbon can be seen for sample B, C and D. Sample C has a large peak at ca. 1530 $cm^{-1}$ associated with disordered sp2 carbon. The nanocrystalline structure of the sample could cause the higher sp2 carbon content due to an increased number of grain boundaries. This peak is also observed in the higher doped grains of sample D. Both spectra for the highly doped sample E show an absence of peaks at approximately 1350 $cm^{-1}$-1580 $cm^{-1}$ suggesting a negligible amount of non-diamond $sp^2$ carbon present at the diamond surface.

Solutions and Materials

All solutions were prepared from Milli-Q™ water (Millipore Corp.), resistivity 18.2M$\Omega$ cm at 25° C. To test the electrochemical characteristics of the boron doped diamond electrodes, solutions comprising potassium hexachloroiridate(IV) (Aldrich Chemical Co), hexaamineruthenium(III) chloride (Strem Chemicals, Newbury Port, Mass.), ferrocenylmethyltrimethylammonium Hexafluorophosphate (made in-house), potassium ferrocyanide (Sigma Aldrich Co), tris(bipyridine)ruthenium(II) chloride (Sigma Aldrich Co), methyl viologen (Sigma Aldrich Co) and iron(II) sulphate (Sigma Aldrich Co), were employed, in 0.1M $KNO_3$ (Fischer Scientific).

Electrode Fabrication—Samples A, B, D and E

In order to fabricate boron doped diamond disc electrodes with well-defined dimensions, a laser micromachiner (E-355H-3-ATHI-O system, Oxford Lasers) was used to cut 1 mm diameter BDD columns (approximately 500 µm thick) from material samples A, B, D and E provided. Sample E is a new polycrystalline boron doped diamond (pBDD) material developed to have very high boron content and very low sp2 content. Prior to further preparation, the boron doped diamond columns were acid cleaned in boiling concentrated $H_2SO_4$ (98%), supersaturated with $KNO_3$. The solution was heated until it was just boiling and the $KNO_3$ had been exhausted (fumes given off turned from brown to white). Once the solution had cooled, the samples were removed, rinsed repeatedly in water and allowed to dry in air. This process removed any non-diamond like carbon that could have been generated during the laser micromachining and also oxygen-terminated the pBDD surface.

In order to utilise the conducting diamond as an electrode, a reliable ohmic connection was made to the back of the BDD columns by sputtering (Edwards E606 sputter/evaporator) a layer of Ti (20 nm), followed by Au (1 µm). The samples were then annealed in a tube oven in air for 4 hours at 400° C. Upon annealing the Ti forms a carbide-based tunneling contact between the diamond and TiC through which carriers can tunnel, lowering the contact resistivity to less than 1 Ωcm. The Au top contact serves as a highly conductive antioxidation layer. A similar method to the standard procedures for sealing metal wires in glass, for the production of metal microelectrodes was adopted in order to insulate the pBDD columns so that only the top (disc) surface was exposed. After sealing the diamond disc in a pulled glass capillary (outer diameter 2 mm, inner diameter 1.16 mm, Harvard Apparatus Ltd, Kent, UK), the pBDD surface was exposed by polishing with carbimet grit paper discs (Buehler, Germany). Electrical contact was made to the pBDD|Au surface using silver epoxy (RS Components Ltd, Northants, UK) and a tinned copper wire used to form an external electrical contact. Finally, epoxy resin (Araldite™, Bostik™ Findley, UK) was placed around the top of the capillary to stabilize the copper wire.

Electrode Fabrication—Sample C and Hydrogen-Terminated Sample B and D

These samples were also initially acid cleaned and then a Ti/Au contact was sputtered as a band onto the top edge of the pBDD. Hydrogen-termination for samples B and D was performed by Bristol University via hydrogen plasma in a CVD reactor at 1 kW and 60 torr. The area for electroanalysis was then masked off using Kapton™ tape (RS Components Ltd, Northants, UK).

Electrochemical Measurements

All electrochemical measurements were made in a three-electrode mode using a potentiostat (CHI730A, CH Instruments Inc. TX) connected to a laptop computer. A saturated calomel electrode (SCE) was used as a reference electrode with a Pt gauze serving as a counter electrode. The laboratory was air conditioned to 23±1° C. for all measurements.

Boron Doped Diamond Electrochemistry

Figure 8:
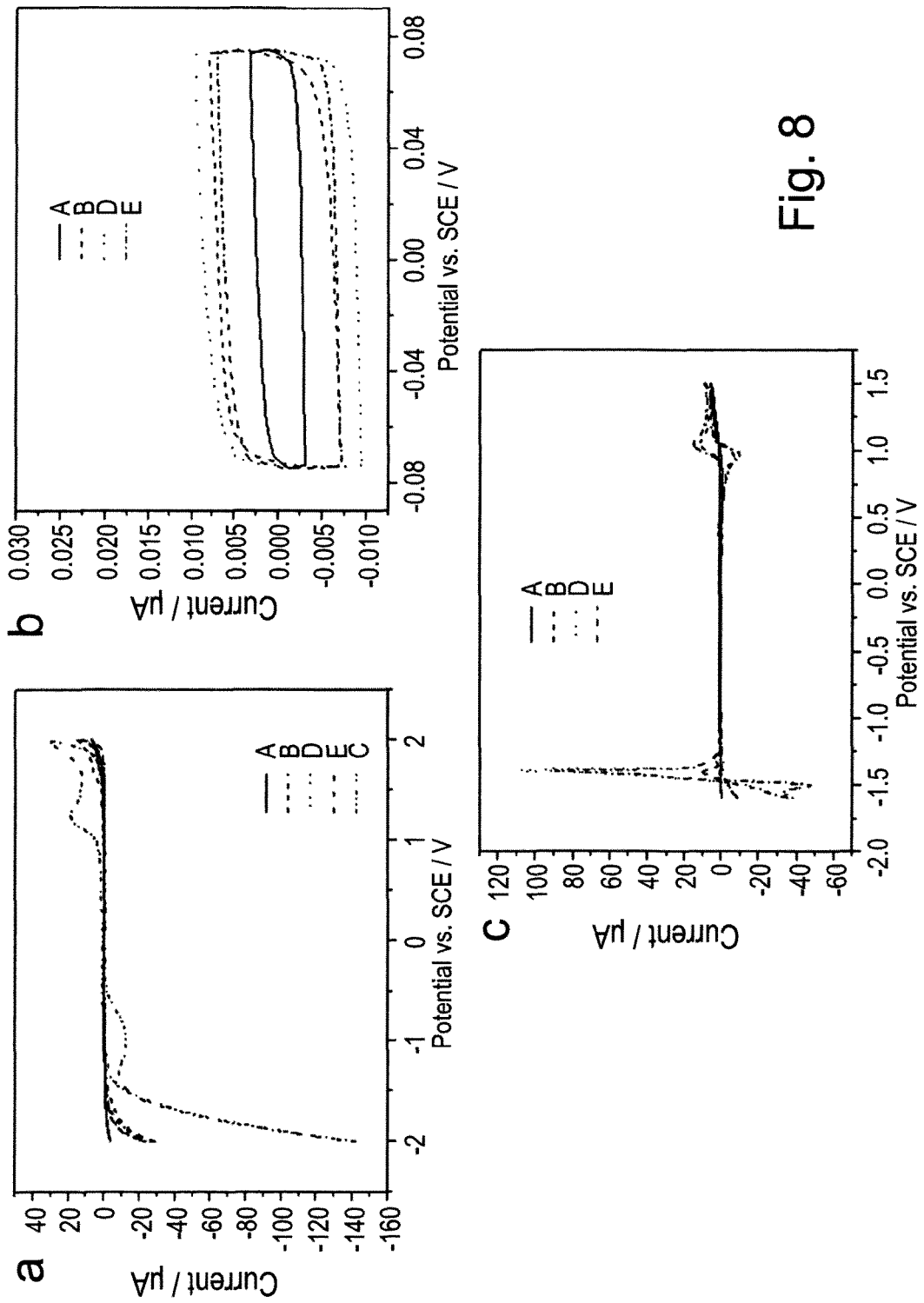
FIG. 8(a) illustrates solvent windows for samples A to E as measured by sweeping a potential of the boron doped synthetic diamond material with respect to a saturated calomel reference electrode in a solution containing only deionised water and 0.1M $KNO_3$ as a supporting electrolyte at pH 6.
FIG. 8(b) illustrates capacitance measurements for samples A, B, D and E, the capacitance measurements being made by sweeping a potential of the boron doped synthetic diamond material with respect to a saturated calomel reference electrode in a solution containing only deionised water and 0.1M $KNO_3$ supporting electrolyte at pH 6 using a scan rate of 100 $mVs^{-1}$.
FIG. 8(c) shows cyclic voltammograms illustrating the electrochemical response of samples A, B, D and E towards the extremes of the solvent window indicating that sample E out-performs the other samples near the extremities of the solvent window, measurements being made by sweeping a potential of the boron doped synthetic diamond material with respect to a saturated calomel reference electrode in a solution containing deionised water, 0.1M $KNO_3$ supporting electrolyte, and 1 mM $Ru(bpy)_3^{2+/3+}$ using a scan rate of 100 $mVs^{-1}$.
FIG. 8(d) illustrates solvent windows for samples A to E which corresponds to FIG. 8(a) but plotted versus current density instead of current.
Figure 8:
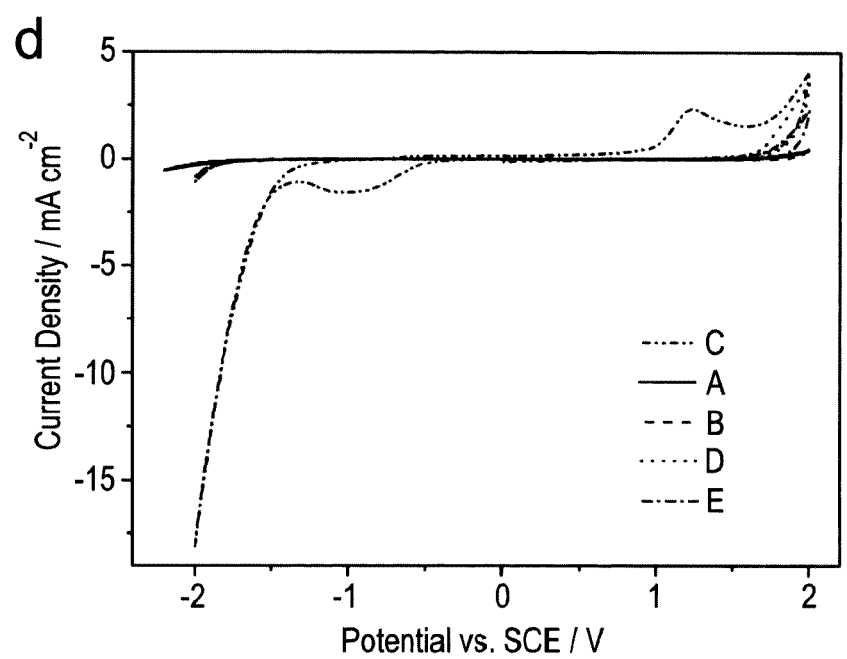

The electrochemical characteristics of the five electrodes were next investigated. All experiments were carried out with a freshly alumina polished and rinsed surface unless otherwise stated. Solvent windows were recorded in 0.1M $KNO_3$ at a scan rate of 100 mV $s^{-1}$ using the fabricated pBDD 1 mm diameter disc electrodes and are shown in FIGS. 8(a) and 8(d). All electrodes exhibited a wide potential window in comparison to other commercially available materials such as Pt and glassy carbon. The electrochemical process of water decomposition defines the range of the solvent window, where hydrogen and oxygen evolution take place at cathodic and anodic extremes respectively and are known to occur via complex mechanisms involving adsorbed intermediates on the electrode surface. In these cases, the activity of the electrode is a function of its surface structure and outer electron configuration e.g. on platinum the intermediates of water electrolysis can chemisorb via partially filled d-orbitals enabling efficient electrolysis. However, for the pBDD electrodes, water decomposition occurs at high potentials, indicating these reactions are likely to be inhibited at the pBDD surface. This is most likely because the surface of the diamond is either hydrogen-terminated by C—H bonds (338 kJ $mol^{-1}$) or, in this case oxygen-terminated with a variety of functional groups containing strong C—O (358 kJ $mol^{-1}$) and C═O bonds (805 kJ $mol^{-1}$). Rearrangement or breaking of these bonds in order to form intermediates is a likely factor in hindering the hydrogen and oxygen evolution reactions.

The widest solvent window is observed for sample A, especially in the cathodic region. As mentioned above, this sample has the lowest boron concentration and conductivity of all the samples, and a limited number of charge carriers at these negative potentials hinders the reduction of water. Wider potential windows for lower doped pBDD in comparison to metallic pBDD have also been observed elsewhere. In contrast, sample C exhibits the narrowest potential window of the five samples, with a large reduction process at −1 V and an oxidation process at 1.2 V. The latter of which can also be seen to a lesser extent for samples B and D at 1.6 V. The onset of a reduction current occurs at −0.4 V suggesting the reduction of oxygen at sp2 carbon. The process observed at positive potentials has been reported previously on pBDD and is attributed to the oxidation of sp2 carbon functionalities. Whilst, sample E is the most highly doped, a wide solvent window is still obtained before water electrolysis occurs, where there are no significant background processes apart from capacitance. The potential windows observed vary in an amount consistent with the species present in the micro-Raman spectra, where sp2 carbon was observed for samples B, C and D but not for sample E which lacks ionisable surface groups.

The solvent window of sample E is featureless over a 3.3 V range between −1.5 and +1.8 V, has no features greater than 0.4 mA $cm^{-2}$ over a range of 3.6 V, and extends out to beyond a range of 4.1 V with no features exceeding 38 mA $cm^{-2}$. Small background features, e.g. below 0.4 mA $cm^{-2}$, are not due to water electrolysis and are most probably due to oxygen or nitrate reduction and surface processes on the diamond surface. It is important to note that high quality boron doped synthetic diamond material according to embodiments of the present invention has very few of these background processes and they do not reach significant magnitudes to adversely affect performance which is a key benefit of the boron doped synthetic diamond material as described herein.

Capacitance values of 3.2, 8.5, 11 and 6.5 µF $cm^{-2}$ were calculated for the pBDD samples A, B, D and E respectively at 0 V vs. SCE in 0.1M $KNO_3$, (approximately an order of magnitude smaller than that expected for Pt) and are shown in FIG. 8(b). The low capacitance of other non-metal electrodes such as highly oriented pyrolytic graphite (HOPG), has previously been attributed to the space charge layer at the electrode/solution interface caused by a low density of states at the Fermi level. A space charge layer is also expected to arise at the pBDD surface. Indeed, comparing the two sp2 carbon free pBDD samples A and E, the capacitance can be seen to increase with increasing boron content and thus density of states. It should be noted that even with a boron content in the metallic conduction regime, a lower capacitance is still observed for sample D in comparison to metal electrodes, indicating a comparatively lower density of states. Samples B and D have unexpectedly high capacitance values when compared to that of the higher doped sample E, most likely due to the presence of sp2 carbon as shown in the micro-Raman and potential windows, for example glassy carbon electrodes are known to have capacitance values in the range 30-40 µF cm$^{-2}$. The capacitance for sample C was much higher in comparison to the other pBDD electrodes, where a value of 35 µF cm$^{-2}$ was calculated. This much higher capacitance could be due to several factors including significant sp2 carbon content, but also a higher surface roughness.

Figure 9:
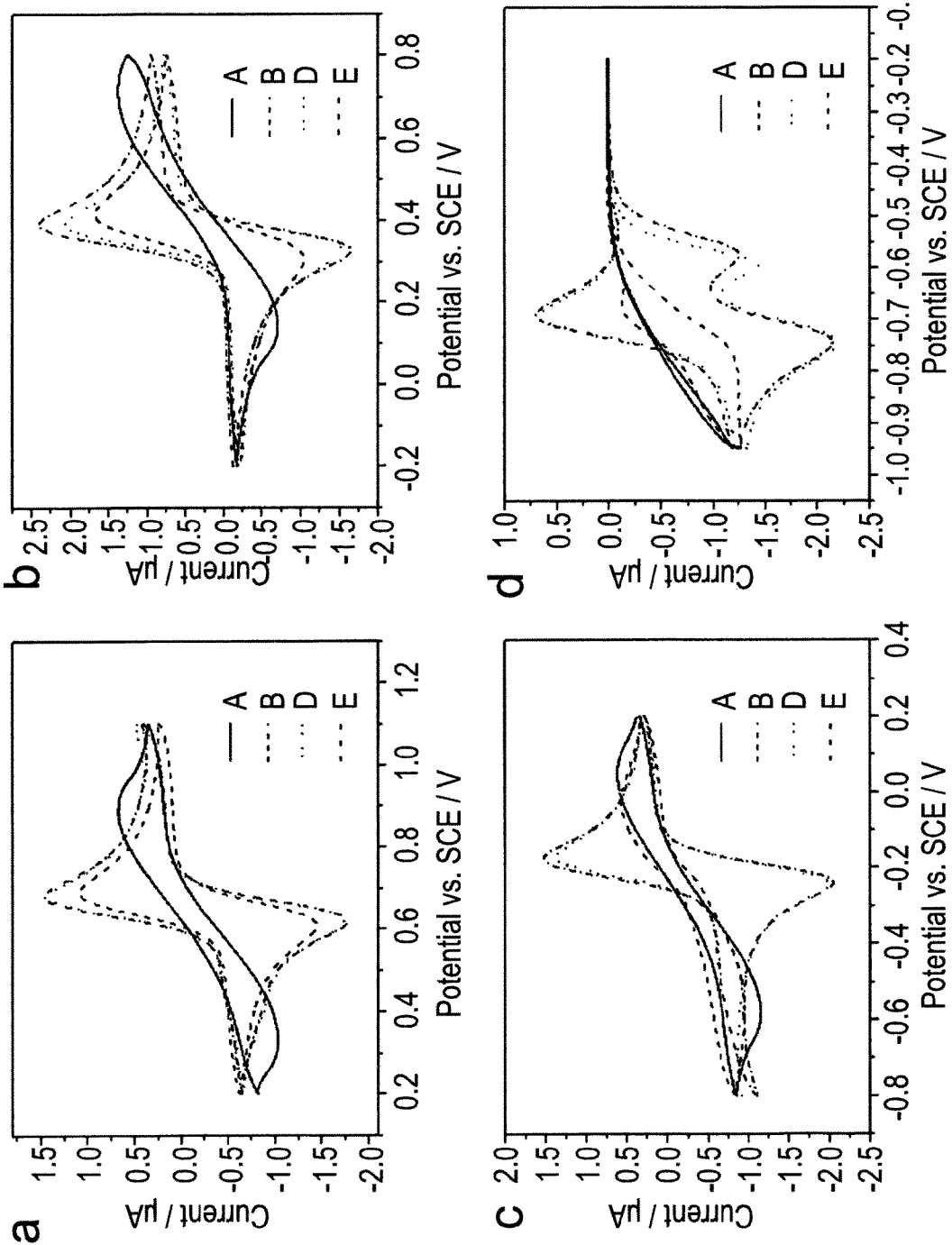
FIGS. 9(a) to 9(d) show cyclic votammograms illustrating the electrochemical response of samples A, B, D and E for a number of outer-sphere redox active species indicating that sample E even out-performs the other samples at central regions within the solvent window, measurements being made by sweeping a potential of the boron doped synthetic diamond material with respect to a saturated calomel reference electrode at a scan rate of 100 $mVs^{-1}$ in a solution containing deionised water, 0.1M $KNO_3$ supporting electrolyte, and (a) 1 mM $IrCl_6^{2-/3-}$, (b) 1 mM $FcTMA^{+/2+}$, (c) 1 mM $Ru\ NH_3)_6^{3+/2+}$, and (d) 1 mM $MV^{2+/1+}$ respectively.

The electrochemical response towards the extremes of the potential window was also investigated for samples A, C and E using 1 mM Ru(bpy)$_3$$^{2+/3+}$ in 0.1M KNO$_3$. FIG. 8(c) shows a reversible single electron oxidation peak at 1.06 V vs. SCE for sample E associated with Ru$^{2+/3+}$ with a $\Delta E_p$ of 59 mV. The reduction of the first bipyridine ligand π* system to [Ru$^{II}$(bpy) (bpy) (bpy$^-$)] can also be seen at −1.5 V vs. SCE on the pBDD electrode. For most other electrode materials, the electrolysis of water does not allow the study of this process in aqueous solutions, and is in fact not observable on sample C, where the reduction of oxygen in the aerated solution masks the signal of interest. The cyclic voltammogram for sample A shows that the same factors that are responsible for the widest potential window and lowest background currents of the five electrodes also hinder the Ru(bpy)$_3$$^{2+/3+}$ redox processes significantly.

pBDD electrodes A, B, D and E were further characterised at varying potentials using a number of outer-sphere redox active species which are unaffected by the chemical functional groups of the conducting surface. These included IrCl$_6$$^{2-/3-}$, FcTMA$^{+/2+}$, RU(NH$_3$)$_6$$^{3+/2+}$ and MV$^{2+/1+}$ as shown in FIG. 9. The voltammetric data for the pBDD electrodes is summarised in Table 1. The reversible nature and kinetics of electron transfer for each species was analysed by comparing the experimental $i_p$ to the theoretical $i_p$ as defined by the Randles-Sevcik equation, $\Delta E_p$ and $k^0$ determined by simulation.

TABLE 1

| | IrCl$_6$$^{2-/3-}$ | | FcTMA$^+$ | | Ru(NH$_3$)$_6$$^{3+/2+}$ | | MV$^{2+/1+}$ | |
|---|---|---|---|---|---|---|---|---|
| | $\Delta E_p$/mV | $k^o$ | $\Delta E_p$/mV | $k^o$ | $\Delta E_p$/mV | $k^o$ | $\Delta E_p$/mV | $k^o$ |
| Sample A | 554 | | 589 | | 642 | | — | |
| Sample B | 80 | | 105 | | 615 | | — | |
| Sample D | 66 | | 65 | | 70 | | 59 | |
| Sample E | 65 | | 62 | | 68 | | 59 | |

It is immediately obvious that sample A has the largest $\Delta E_p$ for all four mediators, ranging from 553 mV for IrCl$_6$$^{2-/3-}$ and increasing as the formal potential of the species becomes more negative, until no diffusion limited response is seen for MV$^{2+/1+}$. While the drawn out cyclic voltammograms are indicative of a resistive response due to the low boron concentration, the electron transfer kinetics are hindered to a greater degree at more negative potentials. This trend reflects the model proposed by Gerischer (*Physical Chemistry, An Advanced Treatise*; Gerischer, H., Ed.; Academic Press, New York, 1970), where the rate of electron transfer at a semi-conductor electrode is proportional to the number of charge carriers available at the redox energy. Therefore, larger $\Delta E_p$ values are observed for sample A than sample B, but both show increased $\Delta E_p$ values for species with negative formal potentials extending further into the band gap, where the electrode depletion layer is greater.

Interestingly, for the highest doped electrodes, samples D and E, the $\Delta E_p$ values are independent of the potential region, but approximately follow the self-exchange rate constant, $k_{exc}$. This is in accordance with the outer-sphere reaction theory for metallic electrodes proposed by Marcus (Marcus, R. A. *The Journal of Chemical Physics* 1956, 24, 966) and indicates that the density of states at these potentials is high enough to facilitate electron transfer at a rate where the rearrangement of the chemical species is now the limiting factor.

Figure 10:
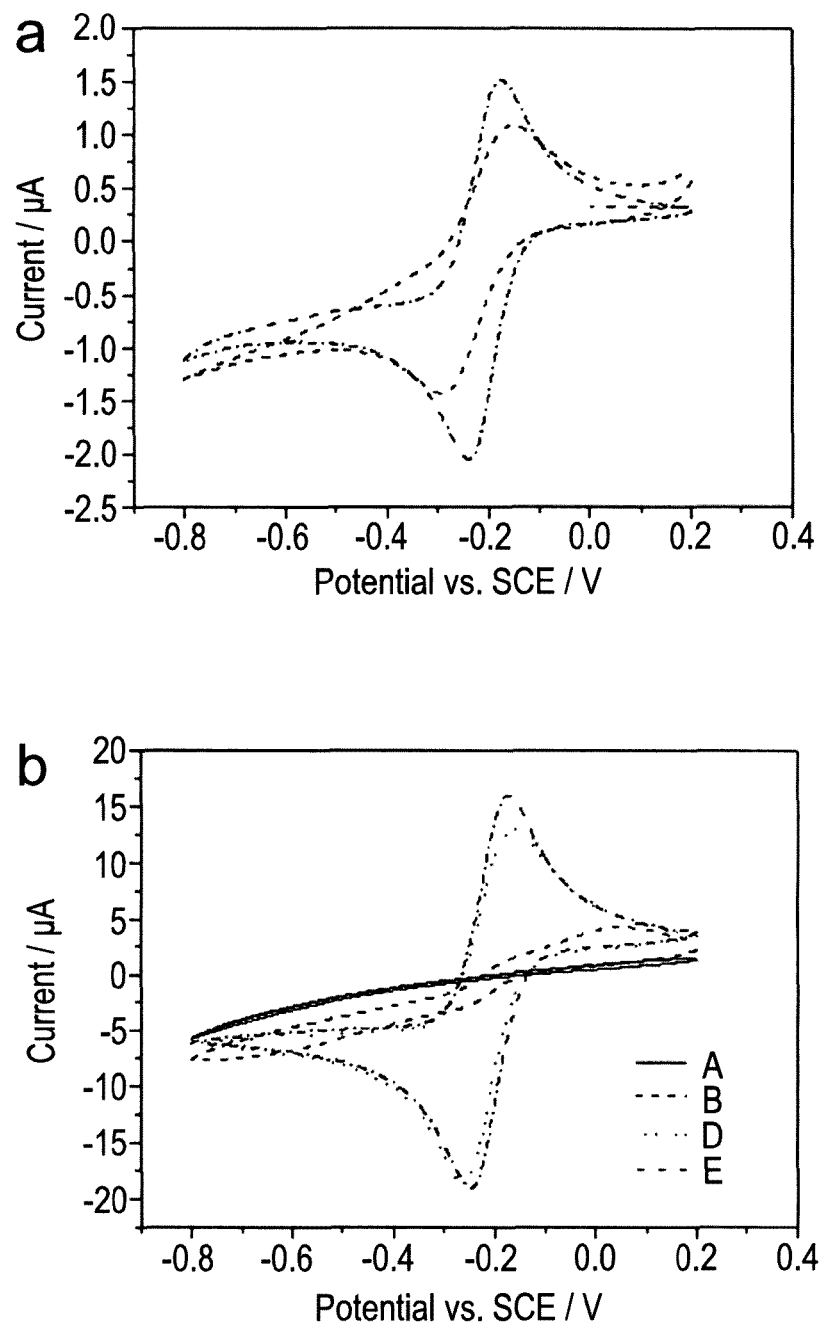
FIG. 10(a) shows cyclic voltammograms for samples B and E for the same outer-sphere redox active species as FIG. 9(c) but with the samples treated so as to be hydrogen terminated—comparison of FIG. 10(a) with FIG. 9(c) indicates that the electrochemical response of sample B is significantly altered by hydrogen termination while sample E remains unchanged.
FIG. 10(b) shows cyclic voltammograms for samples A, B, D and E for the same outer-sphere redox active species as FIGS. 9(c) and 10(a) but with a 10-fold increase in concentration illustrating that sample E has the smallest increase in $\Delta Ep$ with increasing concentration.

It is important to note that the number of charge carriers for a good quality BDD oxygen-terminated electrode is mainly the result of the boron concentration, as exemplified above. However, it is well documented that hydrogen-termination can increase the number of carriers at the diamond/solution interface, therefore increasing surface conductivity. FIG. 10(a) shows the reduction of 1 mM Ru(NH$_3$)$_6$$^{3+/2+}$ for hydrogen-terminated samples B and E. For sample B, a large decrease in $\Delta E_p$ to 140 mV is observed when compared to the oxygen-terminated electrode. This increase in electron kinetics due to the increased density of charge carriers is in accordance with the Gerischer model for semi-conductors. On the other hand, there is no change in the response of sample E between the two types of surface termination, again indicating that the pBDD of sample E has sufficient density of charge carriers to facilitate electron transfer through boron content alone and the kinetics are mainly limited by $k_{exc}$. While the electrochemical response of the semi-conducting pBDD of sample B was improved temporarily through hydrogen-termination, the surface was found to be unstable and was altered after performing cyclic voltammograms up to 1 V, i.e. for IrCl$_6$$^{2-/3-}$, thus losing conductivity.

FIG. 10(b) shows cyclic voltammograms for the reduction of 10 mM Ru(NH$_3$)$_6$$^{3+/2+}$ in 0.1M KNO$_3$ for the four electrodes A, B, D and E. Resistive effects can clearly be seen for samples A and B, where trying to pass such a large current has pushed out the voltammogram. For the higher doped sample D, an increase in $\Delta E_p$ can be seen for the redox couple at the higher concentration i.e. for 100 mV s$^{-1}$, increasing the concentration by an order of magnitude from 1 mM to 10 mM, increases the $\Delta E_p$ values from 70 mV to 110 mV. This effect is much smaller on the highest doped electrode, sample E where $\Delta E_p$ increases from 65 mV to 74 mV. Similar affects are also observed for 10 mM IrCl$_6$$^{2-/3-}$. One possible explanation for this is that increasing concentrations of redox species challenge the pBDD to exchange more charge carriers per unit area. Even for metallic doped pBDD, compared with traditional metallic electrodes, there is a reduced density of states, thus at higher concentrations the ease of electron transfer may be greatly affected. Another possible rationale is that the pBDD has an intrinsic resistance which is governed by the number and mobility of charge carriers. The pBDD sample E used in this work has a resistance of 150 mΩ as determined from four point probe measurements. When the electrode has to pass higher currents, ohmic drop (iR) across the diamond increases, which can affect $\Delta E_p$. However, using Ohms' law, the iR drop at 500 mV s$^{-1}$ for 10 mM solution is calculated as about 6 µV, showing this is unlikely.

Conclusions

The above results indicate that the newly developed polycrystalline boron doped synthetic diamond material of sample E exhibits superior electrochemical performance when compared with samples A to D and that this is linked to the high boron content of the material in combination with the absence of sp2 carbon as measured by Raman spectroscopy. In particular, the material of sample E has been found to possess:

- a solvent window (as measured under conditions of 0.1M KNO$_3$ at pH 6 versus an SCE reference electrode) meeting one or both of the following criteria: (i) extending over at least a potential range of 4.1 V wherein end points of the potential range for the solvent window are defined when anodic and cathodic current density measured at the boron doped synthetic diamond material reaches 38 mA cm$^{-2}$; (ii) extending over at least a potential range of 3.3 V wherein end points of the potential range for the solvent window are defined when anodic and cathodic current density measured at the boron doped synthetic diamond material reaches 0.4 mA cm$^{-2}$;
- a $\Delta E_p$ of no more than 70 mV as measured by sweeping a potential of the boron doped synthetic diamond material at a rate of 100 mV s$^{-1}$ with respect to a reference electrode in a solution containing only deionised water, 0.1M KNO$_3$ supporting electrolyte, and 1 mM of FcTMA$^+$ or Ru(NH$_3$)$_6^{3+}$ at pH 6; and
- a capacitance of no more than 10 µF cm$^{-2}$ as measured by sweeping a potential of the boron doped synthetic diamond material with respect to a reference electrode between 70 mV and −70 mV in a solution containing only deionised water and 0.1M KNO$_3$ supporting electrolyte, measuring resultant current, subtract a current value at 0 V when sweeping towards negative potentials from a current value at 0 V when sweeping towards positive potentials, dividing by 2, and then dividing by an area (cm$^2$) of the boron doped synthetic diamond material and by a rate at which the potential is swept (Vs$^{-1}$) to give a value for capacitance in F cm$^{-2}$.

Further Characterization of pBDD Samples

In order to further characterize the pBDD samples, the materials have been subjected to a relatively new electrochemical imaging technique known as intermittent contact scanning electrochemical microscopy (IC-SECM). In this regard, it is considered that in order to truly understand the electron transfer (ET) characteristics of the electrode/electrolyte interface it is important to be able to spatially map and quantify surface reactivity. Moreover, once the behaviour of the ET electrode system is better understood it is possible to re-engineer the material properties of the electrode in order to maximise ET performance. This is particularly true for polycrystalline boron doped diamond (pBDD) material as the polycrystalline nature of the surface dictates that during the boron doping process different crystallographic grains take up differing amounts of boron resulting in heterogeneous doping of the surface and a variation in the surface electrical properties.

Although different models have been proposed to describe heterogeneous ET (HET) at semi-conducting and metal-like pBDD electrodes there is, as yet, no consensus as to the most realistic model, as it has not yet been possible to investigate how the local dopant density, and particularly the local density of states at the Fermi level (LDOS), influences HET rates on a grain-by-grain basis. Previous attempts to extract HET kinetics at pBDD have used either cyclic voltammetry, which averages over large variations in surface properties, or local techniques, such as scanning electrochemical microscopy (SECM) and fluorescence microscopy. Although significant heterogeneities in HET have been observed by SECM, the spatial resolution has been insufficient to enable measurements to be related directly to grain properties.

Focusing on outer sphere HET, the present inventors have been able to show for the first time that: (i) HET at metal-like pBDD is directly linked to the local doping levels in individual grains; (ii) there is no evidence of any enhancement of HET at grain boundaries; and (iii) HET rates correlate quantitatively with the LDOS in this heterogeneous material. These new insights are not only important in aiding the rational design of electrochemical technologies based on pBDD, but are also of considerable general value in identifying key factors that control HET at solid electrodes.

Solutions, Materials & Electrode Preparation

Aqueous solutions were prepared using Milli-Q™ reagent water (Millipore Corp.). Solutions consisted of 1 mM or 5 mM hexammine ruthenium chloride (Sigma-Aldrich) or 1 mM Ferrocenylmethyltrimethylammonium (FcTMA$^+$) hexafluorophosphate. All solutions contained 0.1M KNO$_3$ (Sigma-Aldrich) as supporting electrolyte. FcTMA$^+$ hexafluorophosphate was prepared via the metathesis of the corresponding iodide salt (99%, Strem) with ammonium hexafluorophosphate (99.5%, Strem).

The pBDD used here was grown using a commercial microwave plasma CVD process (Element Six Ltd., Ascot, UK) and is similar to sample E as previously discussed. That is, the material is a new pBDD material developed to have very high boron content and very low sp2 content. The average boron doping level of this material is about 5×10$^{20}$ atoms cm$^{-3}$, as determined by secondary ion mass spectroscopy. The resulting surface roughness is about 1-2 nm within a grain and 1-5 nm across grains as measured by atomic force microscopy (AFM), with a grain size ranging from 5-40 µm, and a sample thickness of about 500 µm thick.

A 2 mm diameter column of pBDD was cut using a laser micromachiner (E-355H-3-ATHI-O system, Oxford Lasers) and after acid cleaning, an ohmic contact was made to the back of the column by sputtering (Moorfield Minibox) first Ti (20 nm), followed by Au (400 nm). The sample was then annealed in a tube furnace (Carbolite, UK) at 500° C. for 4 hrs to create a titanium carbide contact to the pBDD.

The pBDD sample was contacted to a Ti (20 nm) and Au (400 nm) sputter-coated glass slide using Ag paint (Agar Scientific Ltd., UK), and electrical contact made using wire contacted to the slide, again using Ag paint. Double sided tape (3M) was employed to secure the glass slide onto the base of a Teflon™ SECM cell. The sample was electrically insulated with 5 minute epoxy resin (RS Components, UK) in all areas bar the top surface of the pBDD column.

Microscopy

Micro-Raman spectroscopy (Renishaw InVia, UK) was performed using a 514.5 nm Ar$^+$ laser with a CCD detector (Peltier cooled). The spectrometer was equipped with an 1800 lines/mm diffraction grating. Maps were created by using an automated stage (incremental step size of 1.2 µm) where the laser beam was focussed with a 100× objective. A peak shift at approximately 1332 cm$^{-1}$ was analysed (Wire 3.0).

Field emission-scanning electron microscopy (FE-SEM) was performed using a Zeiss Supra 55V. 2 kV was applied and an in-lens detector was used for the micrographs in this work.

Electrochemical Measurements

Pt disk UMEs (1-1.3 μm in diameter) were fabricated in-house from Wollaston wire using established procedures. The size of the electrode was determined by recording the steady-state current for electrolysis of a known concentration of redox active mediator in solution. All of the IC-SECM images in this work were obtained by taking a reading every 2 μm (the step size) with a sub-step (how often the tip is repositioned during scanning—'feeling' the substrate) every 0.25 μm.

All electrochemical measurements were performed using a saturated calomel electrode (SCE) as the reference and a Pt wire for the counter, and a potentiostat (Model CH760C, CH instruments).

Figure 11:
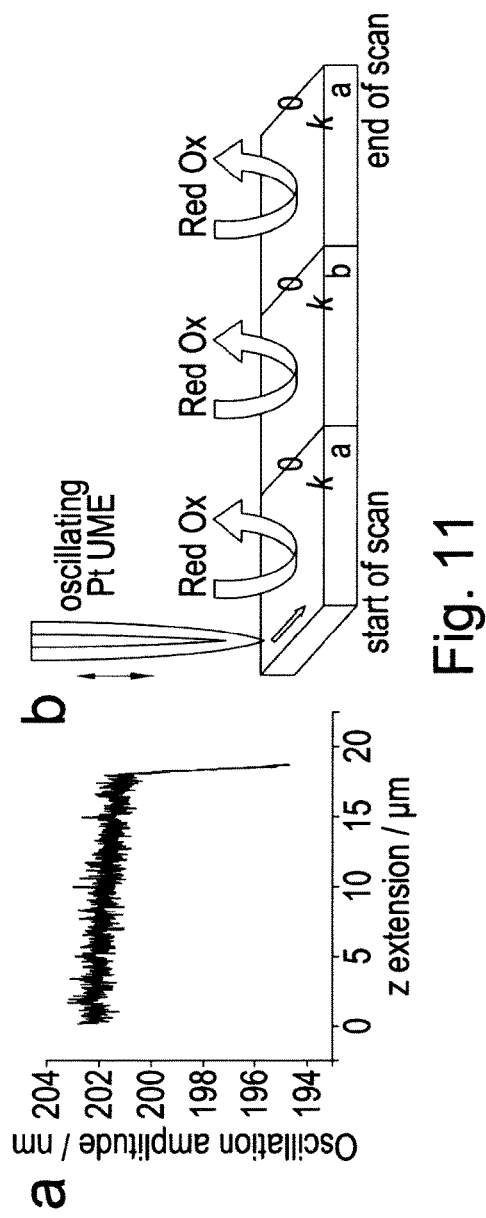
FIG. 11(a) shows an example of a piezoelectric oscillation signal from an intermittent contact scanning electrochemical microscope (IC-SECM) used to analyse the microstructural properties of sample E.
FIG. 11(b) shows a schematic illustrating the IC-SECM technique applied to quantifying electron transfer kinetics at the surface of sample E.

In brief, during IC-SECM, the oscillation amplitude of the tip UME is kept fixed at a constant damped value, associated with tip to surface contact, as shown in FIG. 11(a) which shows how the free oscillation (oscillation frequency=80 Hz) of a=1.3 μm diameter disk Pt UME, RG=10, changes as the tip approaches and then contacts the surface of pBDD the sudden decrease in oscillation amplitude indicates contact of the tip with the surface. Note that as it is practically near impossible to obtain perfect alignment between tip and pBDD material, contact is likely from an edge of the glass sheath surrounding the Pt disc UME. This is in general preferred as it avoids direct pBDD to tip electrode contact, resulting in possible shorting. During imaging, the tip scans one line in "contact" with the surface, collecting information not only on the tip current signal but also on the pBDD topography (via the distance the tip needs to move in order to keep the damped oscillation constant). On the pass back the tip can be set to acquire current data at a distance defined by the user and pertinent to the size of electrode employed.

FIG. 11(b) shows a schematic highlighting application of IC-SECM to a heterogeneously active pBDD surface in pBDD generation—tip collection mode. Different grains contain different boron dopant levels, each characterised by an intrinsic rate constant, $k^0$. Furthermore, non-diamond like impurities, if present, will also show ET activity characterised with their own $k_0$.

Figure 12:
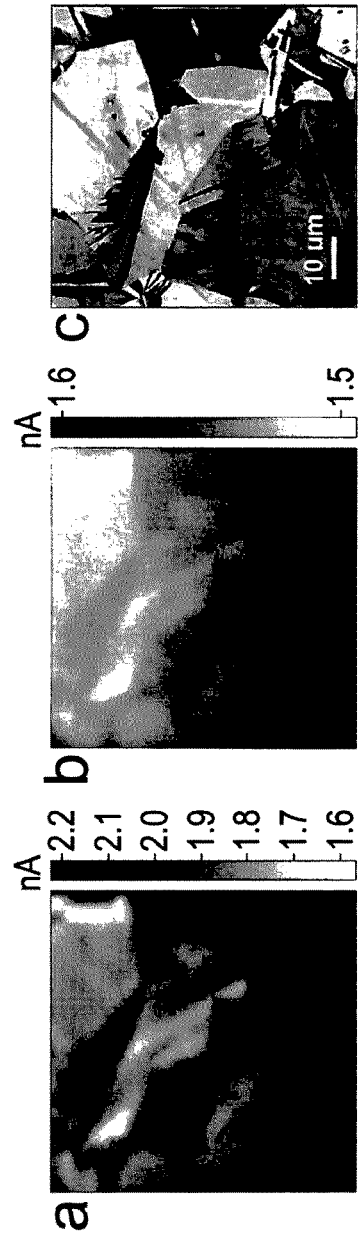
FIGS. 12(a) and (b) show 70 µm×70 µm IC-SECM images for the collection of 5 mM $Ru(NH_3)_6^{2+}$ electrogenerated at the surface of sample E (held at −0.4 V) with varied tip-sample separation: (a) 1 µm; and (b) 2 µm.
FIG. 12(c) shows a corresponding field emission scanning electron micrograph (FE-SEM) for the same region of material as imaged in FIGS. 12(a) and (b)

FIG. 12 shows typical 70 μm×70 μm IC-SECM SG-TC images of the pBDD surface for the tip collection of 5 mM $Ru(NH_3)_6^{2+}$ at fixed d values of: (a) 1 μm; and (b) 2 μm. The substrate is biased at −0.4 V (η=−0.138 V) versus a silver-silver chloride electrode (Ag/AgCl) to drive $Ru(NH_3)_6^{3+}$ reduction, whilst the tip was held at 0.0 V versus Ag/AgCl to collect $Ru(NH_3)_6^{2+}$ at a diffusion-limited rate. Also displayed is a FE-SEM image (FIG. 12(c)), recorded at 2 kV, in the same area of the IC-SECM scan. Previous EM studies (Tenne, R.; Patel, K.; Hashimoto, K.; Fujishima, A. *J. Electroanal. Chem.* 1993, 347, 409) have shown that secondary electron emission yields from BDD reach a maximum at boron concentrations of >$10^{19}$ cm$^{-3}$, thus the darker areas in the image represent zones which contain more boron. The FE-SEM image of the polished pBDD surface (~1-2 nm surface roughness within a grain and ~1-5 nm across grains as revealed by AFM) shows that the surface is heterogeneously doped, with certain grain structures taking up less boron than surrounding areas.

Clearly evident is the close correlation between the FE-SEM image of the grain structure FIG. 12(c) and the IC-SECM tip current map of the surface electroactivity (especially in FIG. 12(a)). Electrochemical images which clearly reveal grain structure have never been observed before during the electrochemical mapping of pBDD. Even subtle current differences within grains are apparent. In essence, qualitatively, the areas which contain higher levels of boron show enhanced tip current, i.e. increased electroactivity. It is also clear that the electrochemical resolution of the image is enhanced by employing smaller tip-substrate imaging separations and highlights one of the advantages of this technique, i.e. the ability to accurately control and maintain the tip-substrate separation. This is essential when using high resolution tips where even a difference in d of 1 μm makes an enormous difference to the resolution of the electrochemical image as evidenced by the difference between FIGS. 12(a) and (b).

Previous SECM studies have associated increased areas of current with either areas of inter-granular non-diamond-like (sp$^2$) carbon or metallic-like regions of the surface. From these images it is already strikingly clear that the variations in current magnitude are predominantly associated with the grain structure of the surface and hence boron dopant levels. Further information on boron dopant levels and the presence of sp$^2$ carbon contaminants was obtained by recording micro-Raman maps of the surface in the same area as the IC-SECM images.

Figure 13:
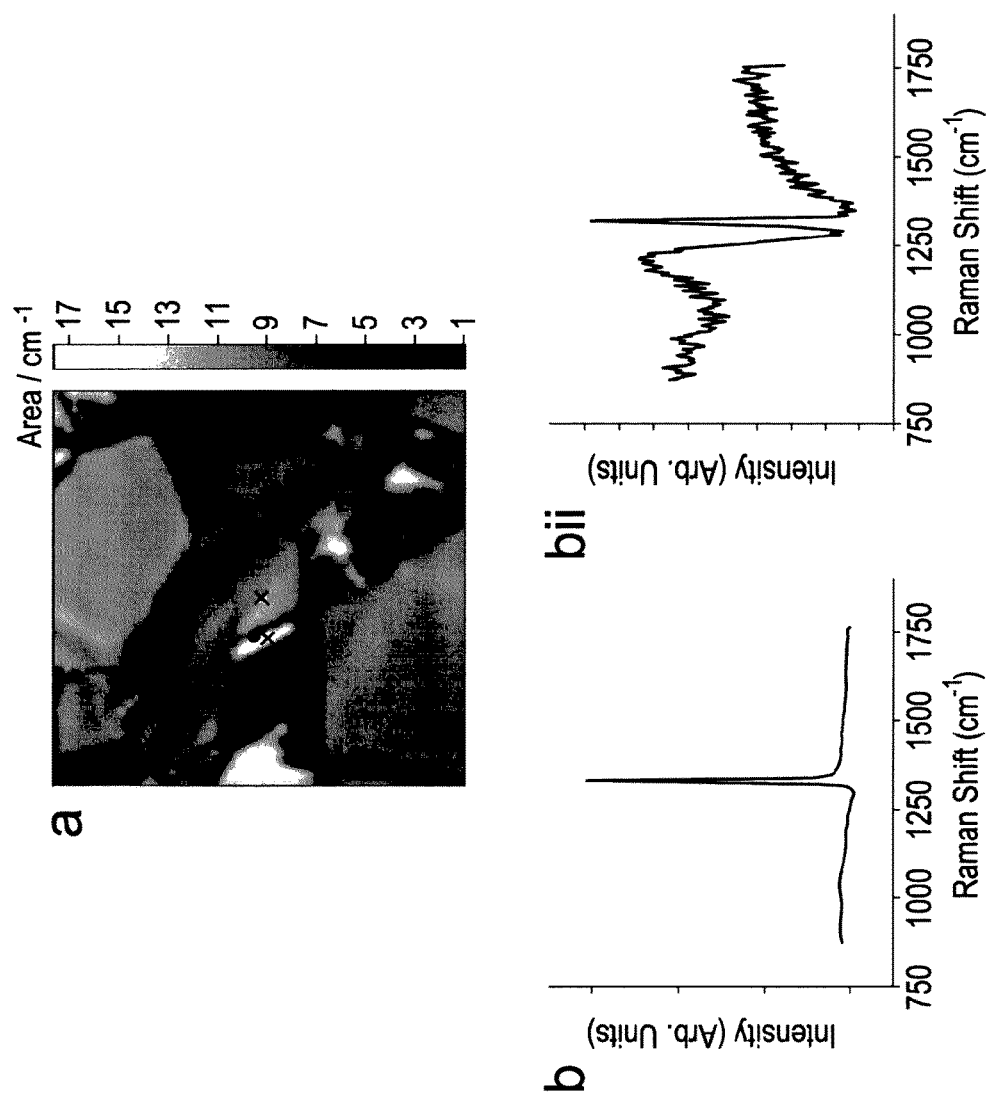
FIG. 13(a) illustrates a Raman map showing the integrated area under the peak for the zone centre optical phonon (~1332 $cm^{-1}$) for the same region of material as imaged in FIGS. 12(a) to (c) with darker areas indicating more boron dopant—by comparing images it can be seen that the grain structure shown in the FE-SEM image of FIG. 12(c) can be correlated with the electrochemical map shown in FIG. 12(a) and the Raman map shown in FIG. 13(a)
FIGS. 13(b) and (bii) illustrate Raman spectra from regions of lowest boron concentration and highest boron concentration respectively in the Raman map shown in FIG. 13(a)

FIG. 13(a) shows a Raman map for the integrated area under the peak for the zone centre optical phonon (~1332 cm$^{-1}$) associated with sp$^a$ carbon. As the boron concentration increases the peak shifts to lower wavenumbers, with a smaller integrated peak area. For the image in FIG. 13(a), a Raman spectrum was recorded at every 1.2 μm over the wavenumber range 900-1800 cm$^{-1}$. The spot size employed was <5 μm; however the intensity of this is much greater in the centre. The darker zones in the image are thus associated with higher boron content and correlate with the data recorded in FIG. 12.

To provide further information on the boron doping levels, individual spectra were analysed in regions of the sample which contained the lowest and highest boron levels. Both spectra (FIGS. 13(bi) and (bii)) show a diamond (sp$^3$) peak centred at 1332 cm$^{-1}$, the asymmetry of the peak (Fano resonance) indicates that in both areas the boron concentration, [B], must be ≥$10^{20}$ atoms cm$^{-3}$. As the boron concentration increases the peak becomes more asymmetrical. In terms of electrical characteristics, p-type semi-conducting behaviour is expected for [B]<$1×10^{19}$ atoms cm$^{-3}$, as [B] increases from approximately $1×10^{19}$-$1×10^{20}$ cm$^{-1}$ electrical conduction is via a hopping mechanism, until at [B]≈$1×10^{20}$ atoms cm$^{-3}$ the material exhibits metal-like conductivity. Hence the boron concentration is not low enough for any region of the sample to be considered truly semi-conducting. Also important, in FIG. 13(bi) is the absence of a peak associated with non-diamond-like sp$^2$ carbon at about 1350-1580 cm$^{-1}$. Spectra displayed in FIGS. 13(bi) and 13(bii) show no evidence of non-diamond carbon. As sp$^2$ carbon has also been previously associated with grain boundaries, spectra were also analysed for at least 10 grain boundaries in FIG. 13(a). None displayed any evidence of significant sp$^2$ carbon.

Figure 14:
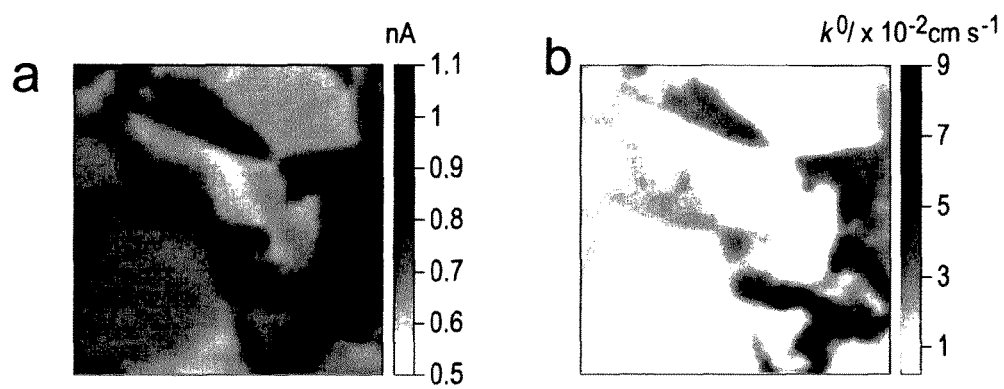
FIG. 14 illustrates an IC-SECM map of: (a) tip currents; and (b) corresponding $k^0$ values for the same region of material as previously depicted using 5 mM $Ru(NH_3)_6^{2+}$ in 50 mM $KNO_3$, electrogenerated at the surface of the pBDD (at an overpotential η=−0.004 V), using a 2 µm tip electrode and a tip-pBDD separation of 1 µm.

Finite element simulations were employed to quantify tip currents in terms of $k^0$ using Butler-Volmer kinetics. FIG. 14(b) shows the resulting $k^0$ map as a function of tip x,y position, for a fixed d of 1 μm, extracted from the raw limiting current data shown in FIG. 14(a). This is the first time that SECM has been utilised to extract $k^0$ on a point-by-point basis on a heterogeneously active electrode surface. This is only possible as the tip-substrate separation is unambiguously known at all points during the scan. In FIG.

14(b), $k^0$ ranges from a value of 3.3 (±1.5)×10$^{-2}$ cm s$^{-1}$ (high boron) to 0.7 (±0.3)×10$^{-2}$ cm s$^{-1}$ (low boron).

Figure 15:
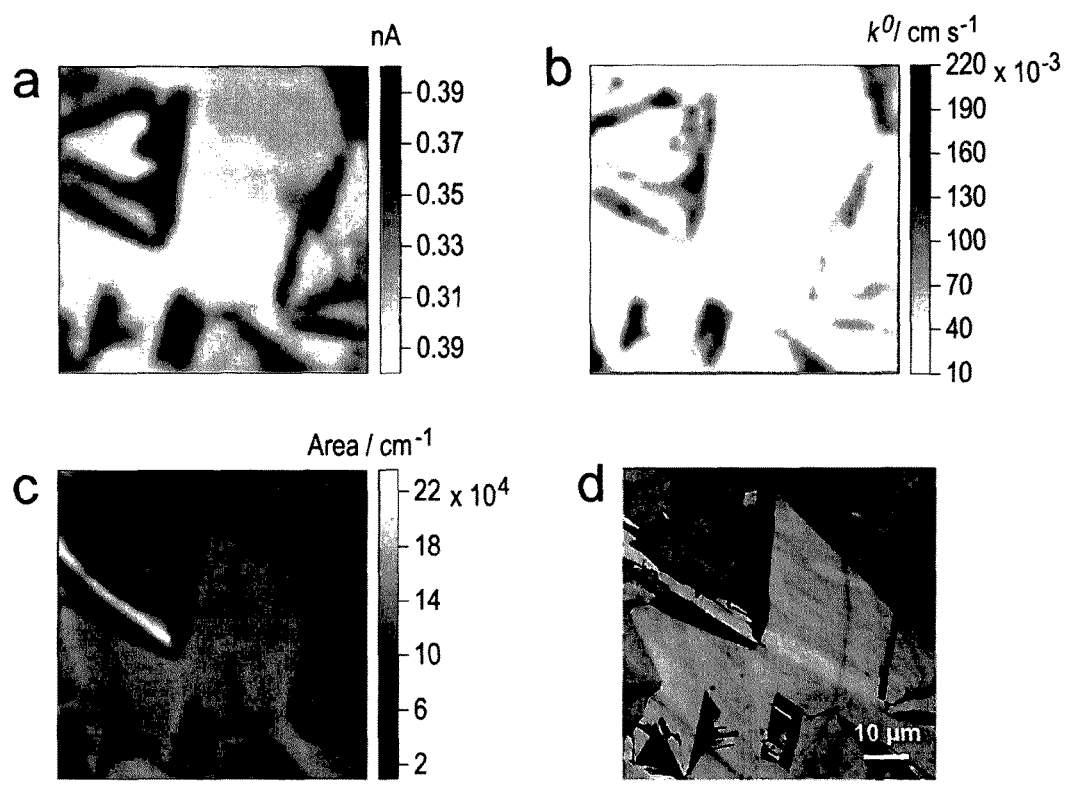
FIG. 15 shows various images of the same portion of material including: (a) a 70 µm×70 µm IC-SECM image for the collection of 1 mM $FcTMA^{2+}$ electrogenerated at the surface of boron doped diamond material with the material held with an overpotential $(E-E_0)$ of 0.045 V; (b) a $k^0$ map calculated using finite element simulations; (c) a Raman map to show the integrated area of the 1332 $cm^{-1}$ peak; and (d) an FE-SEM image.

To further investigate HET rates at pBDD electrodes, FcTMA$^{+/2+}$ was employed as the redox couple. This was chosen as it has been used extensively for the investigation of electrode kinetics at carbon-based electrodes and the formal potential, $E^{o'}$, for FcTMA$^{+/+}$ is considerably more positive by about 0.55V than for Ru(NH$_3$)$_6$$^{3+}$. The power of the approach is that both FE-SEM and Raman images, FIGS. 15(d) and (c), respectively, were recorded in the same area as the IC-SECM image (FIG. 15(a)) to allow direct correlation of electrochemical activity with doping levels. In this case, the bulk solution contained 1 mM FcTMA$^+$ (50 mM KNO$_3$) and a tip of a=1.3 µm, d=1.0 µm was employed, with the substrate biased at a potential of +0.420 V versus Ag/AgCl (sat. KCl) (r=0.045 V) to oxidise FcTMA$^+$ whilst the tip was biased at 0.0 V to collect any FcTMA$^2$ generated at the pBDD substrate at a diffusion-controlled rate. Distinct zones of tip current activity are again observed which correlate precisely with the areas of high and low dopant concentrations. The corresponding $k^0$ map, shown in FIG. 15(b), further highlights the contrasting electrochemical activity between different characteristic grains and analysis of $k^0$ for the two differently doped regions yielded 9.7 (±0.4)×10$^{-2}$ cm s$^{-1}$ (high) and 2.2 (±0.8)×10$^{-2}$ cm s$^{-1}$ (low).

The data suggest that on both grain types (high and low-doped), $k^0$ for FcTMA$^{+2/2+}$ is approximately 3-fold higher than for RU(NH$_3$)$_6$$^{3+/2+}$. This is qualitatively consistent with the higher self-exchange rate constant for FcTMA$^{+/2+}$. Perhaps most interesting is that the ratio of the high to low $k^0$ values, associated with each grain type, is similar (approximately 4-5) for both redox couples. To explore the reasons for this behaviour, information on the LDOS of the two characteristic grain types were sought via local capacitance measurements. Measuring capacitance on the microscale by electrochemical methods is challenging due to the small signals that result, compared to those from sources of stray capacitance, which must be minimized. Photolithographic techniques have previously been employed for the measurement of the quantum capacitance of graphene, however such an approach would not be easily applicable to the pBDD samples, due to the irregular spacing and geometry of the high and low-doped grains. Thus, the present inventors have chosen to use scanning electrochemical cell microscopy (SECCM), as a new approach for high spatial resolution capacitance measurements.

Figure 16:
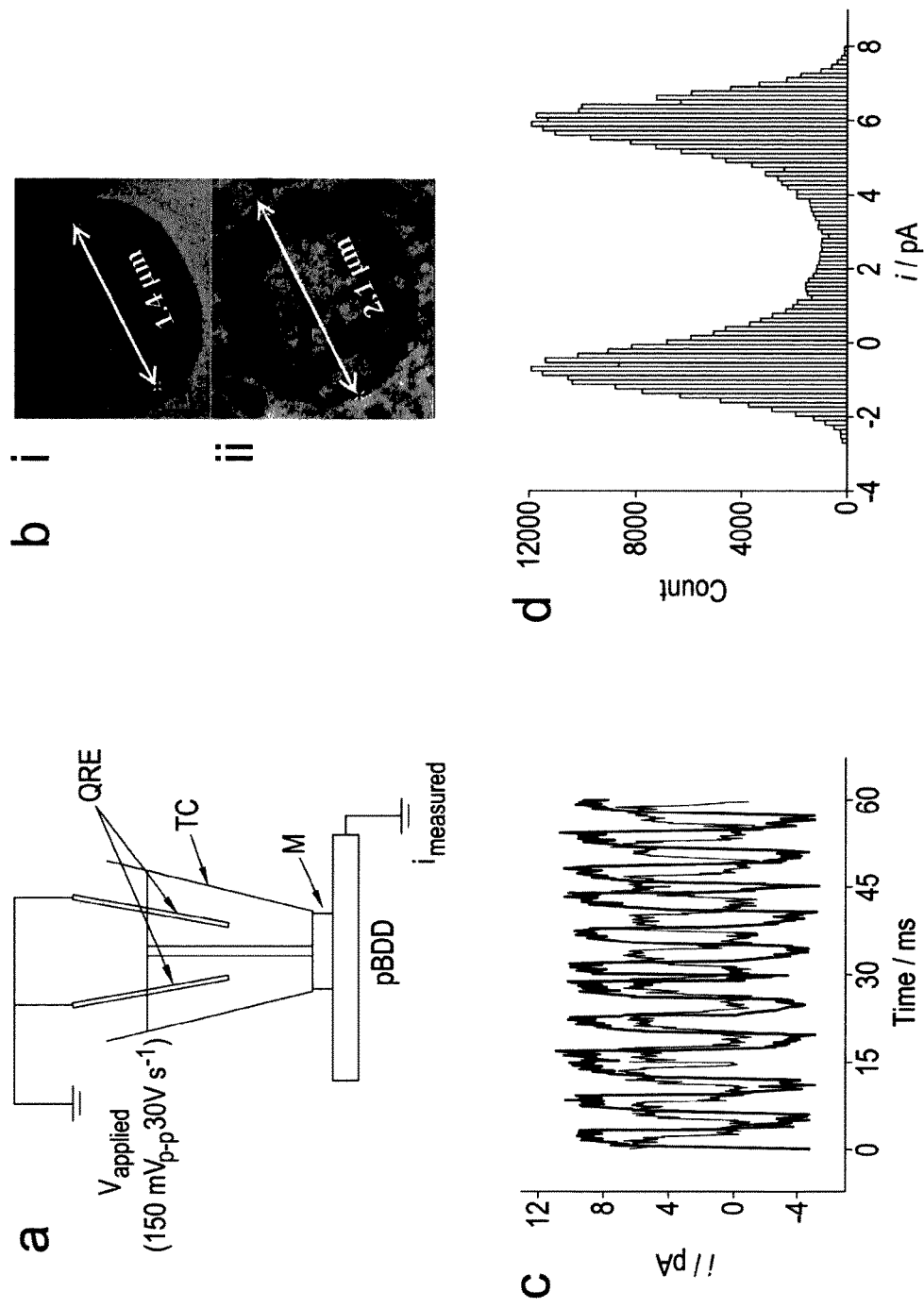
FIG. 16 shows examples of capacitance measurements: (a) schematic showing the scanning electrochemical cell microscopy set-up for recording micron-scale capacitance; (b) typical FE-SEM images of (i) the end of the pulled theta capillary and (ii) salt remaining after the meniscus has been in contact with the substrate; (c) typical capacitance measurements in high (black) and low (red) doped region of the substrate, in 0.05M $KNO_3$; and (d) histogram plot of the currents recorded during one typical i-t trace lasting approximately 45 seconds.

A schematic of the SECCM set-up is shown in FIG. 16(a). The probe consisted of a tapered theta glass capillary (TC), drawn to a tip of size ~1.5 µm. Each chamber of the pipet was filled with electrolyte solution and contained a chloride-coated silver wire which functioned as a quasi-reference counter electrode (QRE). For these measurements, an electrochemical cell was made when the meniscus (M) at the end of the solution-filled capillary made contact with the pBDD substrate working electrode; grounded and under ambient conditions. FIG. 16(b) shows typical FE-SEM images of: (i) the theta glass capillary end; and (ii) an imprint from the residue left from the meniscus contact, defining precisely the electrode area, A. Capacitance measurements were made over characteristic high and low-doped regions of the surface, identified by optical microscopy in-situ with SECCM (with the low doped grains appearing brighter). A 0.150 V peak-to-peak triangular wave centred on 0.000 V, scan rate v=30 V s$^{-1}$, was applied between the QREs. The corresponding square-wave current time response was diagnostic of a capacitive charging response for the two differently-doped regions of the pBDD surface. FIG. 16(c) illustrates typical responses which show clearly that the current amplitude, $i_{amp}$, reflects the doping level. FIG. 16(d) shows a typical histogram of the currents measured at the pBDD electrode in the two different regions where the modal values represent a maximum and minimum of the $i_{amp}$–t square wave response. The capacitance is extracted as $C_{meas}=i_{amp}/2vA$. Mean capacitance values were calculated to be 5.2±0.8 µF cm$^{-2}$ and 3.1±0.4 µF cm$^{-2}$ in the high and low doped regions, respectively.

For pBDD, $C_{meas}$, has contributions from the Helmholtz capacitance, $C_H$, the diffuse layer capacitance, $C_{diff}$, and the capacitance of the space charge region, $C_{sc}$, even when diamond is doped sufficiently to be considered metal-like, because pBDD has a limited density of charge carriers compared to a typical metal. Thus, as for other carbon materials such as highly orientated pyrolytic graphite and single walled carbon nanotubes, the capacitance can be written as:

$$C_{meas}^{-1}=C_H^{-1}+C_{Diff}^{-1}+C_{SC}^{-1} \quad (2)$$

Under the high ionic strength conditions in these studies, $C_{diff} \gg C_H$ and so contributes negligibly to $C_{meas}$.

$C_{sc}$ is related to the LDOS at the Fermi level, $D(E_f)$ by:

$$C_{SC}=e_o\sqrt{(\varepsilon\varepsilon_o D(E_f))} \quad (3)$$

where $e_o$ is the electronic charge, $\varepsilon$ is the dielectric constant of pBDD (5.5) and $\varepsilon_o$ is the vacuum permittivity. Assuming a typical value of $C_H \approx 20$ µF cm$^{-2}$, the LDOS for the high and low boron doped grains is estimated as ~1.7 (±0.02)×10$^{20}$ cm$^{-3}$ eV$^{-1}$ and ~7.5 (±0.08)×10$^{20}$ cm$^{-3}$ eV$^{-1}$ respectively, i.e. there is a difference of a factor of ~4-5 in the LDOS. For comparison, metals have $D(E_f)$~10$^{23}$ cm$^{-3}$ eV$^{-1}$.

The ratio of LDOS in the high and low boron doped grains correlates with the ratio of $k^0$ values measured for in these domains for each of the two different outer sphere redox couples. Thus, for this relatively highly-doped carbon material, it is evident that the HET kinetics is governed to a large extent by the LDOS, which in turn is controlled by boron concentration. This produces a clear pattern of spatial HET activity in which rates are determined by the characteristics of particular grains and not by boron or sp$^2$ carbon accumulation at grain boundaries. These new insights into the control of HET at an electrode surface should not only be of fundamental value, but also aid in the development and optimisation of emerging conducting diamond electrochemical technologies.

Conclusions

The new polycrystalline boron doped synthetic diamond material comprises no sp2 carbon as detectable by Raman spectroscopy, even in grain boundary regions. Furthermore the boron concentration is such that on the surface of the material a majority of the grains have a boron concentration in a range 1×10$^{20}$ boron atoms cm$^{-3}$ to 7×10$^{21}$ boron atoms. It has thus been shown that polycrystalline boron doped synthetic diamond material having improved electrochemical functionality can be provided by a material which comprises substantially no sp2 carbon and includes a majority of surface grains exhibiting metallic conduction in the boron concentration range 1×10$^{20}$ boron atoms cm$^3$ to 7×10$^{21}$ boron atoms.

Single Crystal Boron Doped Diamond (scBDD) Materials

A series of single crystal synthetic diamond samples were fabricated comprising a support substrate layer having a boron content of approximately 10$^{19}$ atoms cm$^{-3}$ and a thin capping layer having a higher boron content which was varied from sample to sample. Boron content within the capping layer was measured by SIMS as previously described. An electrochemical electrode was fabricated for each sample in a similar manner to that described previously for the pBDD samples. All samples were treated so as to be oxygen terminated as previously described.

$\Delta E_p$ was then measured for each sample by sweeping the boron doped synthetic diamond electrode at a rate of 100 mV s$^{-1}$ with respect to a reference electrode in a solution containing only solvent (deionised water), 0.1M supporting electrolyte (KNO$_3$), and 1 mM of a redox active species (FcTMA$^+$ at pH 7).

It was found that $\Delta E_p$ was too high for samples in which the capping layer has a boron content below the limit for metallic conduction of 1×10$^{20}$ atoms cm$^{-3}$. As the boron content is increased it was found that the over-potential decreases towards the limit of ideal behaviour of 59 mV. However, it was found that the solvent window decreases as the boron concentration increases and the capacitance increases. Accordingly, it was found that while increasing the boron content is advantageous for reducing the over-potential, boron concentrations below 7×10$^{21}$ atoms cm$^{-3}$ are desirable to ensure that the solvent window remains sufficiently broad and the capacitance remains sufficiently low. A suitable single crystal synthetic diamond sample comprising a support substrate layer having a boron content of approximately 10$^{19}$ atoms cm$^{-3}$ and a capping layer having a boron content of approximately 1-2×10$^{21}$ atoms cm$^{-3}$ was found to have a solvent window, $\Delta E_p$, and capacitance as required by embodiments of the present invention.

Following on from the above work, a series of bulk boron doped single crystal samples have been fabricated analysed in an analogous manner to that described above for the capped samples. It has been found that the bulk boron doped single crystal samples follow a similar pattern. That is, increasing the boron content advantageously reduces $\Delta E_p$ but detrimentally reduces the solvent window and increases capacitance. Again, it was found that a balance can be found by selecting a boron content within a range 1×10$^{20}$ atoms cm$^{-3}$ to 7×10$^{21}$ atoms cm$^{-3}$. For example, a bulk boron doped single crystal synthetic diamond material having a boron content of 1.22×10$^{21}$ atoms cm$^3$ was found to have a mean FcTMA$^+$ $\Delta Ep$ of 66.8 mV, a capacitance of 7 µF cm$^{-2}$, and a solvent window over a potential range −2.1V to +2.3V. As previously described in the synthesis section, the material is also required to be of high crystalline quality in addition to achieving the correct boron concentrations in order to achieve these electrochemical characteristics.

In addition to the above, single crystal boron doped diamond materials according to embodiments of the present invention have been used to investigate the effects of crystallographic orientation and surface termination on electrochemical performance for inner-sphere reactions. Throughout literature the most common surface terminations for BDD electrodes are hydrogen- and oxygen-terminations. As previously mentioned, for metallically doped BDD, surface termination has been shown to have very little impact on electron transfer kinetics for outer-sphere redox species. However, extensive studies with inner-sphere redox species, such as Fe(CN)$_6^{3-/4-}$, on traditional electrode materials have shown a complex electrochemical response dependent on the electrode material, as well as supporting electrolyte type, redox species concentration and surface chemical state/functionalities (see, for example, Shakkthivel, P.; Chen, S.-M. *Biosens. Bioelectron.* 2007, 22, 1680 and Pihel, K.; Walker, Q. D.; Wightman, R. M. *Anal. Chem.* 1996, 68, 2084). Several papers have presented voltammetry of Fe(CN)$_6^{3-/4-}$ at highly and heavily boron doped pBDD electrodes where it is suggested that electron transfer kinetics are slower at an oxygen-terminated pBDD surface in comparison with hydrogen-terminated samples (see, for example, Granger, M. C., Swain, G. M. *J. Electrochem. Soc.* 1999, 146, 4551, Boukherroub, R., Wallart, X., Szunerits, S., Marcus, B., Bouvier, P., Mermoux, M. *Electrochem. Commun.* 2005, 7, 937, Actis, P., Denoyelle, A., Boukherroub, R., Szunerits, S. *Electrochem. Commun.* 2008, 10, 402, and Marken, F., Paddon, C. A., Asogan, D. *Electrochem. Commun.* 2002, 4, 62). In contrast, a number of studies have found that after anodic pretreatment of pBDD, an increase in charge transfer was achieved i.e. $\Delta E_p$ values decreased from 200 to 90 mV (see, for example, Prado, C.; Wilkins, S. J.; Marken, F.; Compton, R. G. *Electroanalysis* 2002, 14, 262 and El Tall, O.; Jaffrezic-Renault, N.; Sigaud, M.; Vittori, O. *Electroanalysis* 2007, 19, 1152). The effect of surface termination on electron transfer kinetics of Fe(CN)$_6^{3-/4-}$ has been attributed to several factors including the potential of the reaction plane, this is where the negative charge on the oxygen containing groups can repel negatively charged redox species. Site-blocking oxygen functional groups have also been suggested as inhibiting electron transfer.

The functional groups which reside on the diamond surface are dependent on crystal orientation and the method of termination. The oxidation of Fe(CN)$_6^{3-/4-}$ at a polycrystalline surface as well as single crystal surfaces which have been oxygen-terminated via two different methods have been investigated. First, FIG. 17(ai) shows cyclic voltammograms for the oxidation of 1 mM Fe(CN)$_6^{3-/4-}$ in 0.1M KNO$_3$ at metallically doped pBDD, {100}, {110} and {111} single crystal BDD, where the diamond is oxygen-terminated via acid boiling and subsequent alumina polishing. All four electrodes give $\Delta E_p$ values close to reversible, i.e. about 62 mV to 70 mV. The wave shapes indicate fast electron kinetics (i.e. diffusion control) for the redox electrochemistry of Fe(CN)$_6^{3-/4-}$ at alumina polished BDD of all crystal faces. Previous studies by McEvoy have shown improved kinetics for Fe(CN)$_6^{3-/4-}$ at alumina polished BDD electrodes, but was explained in terms of hydrocarbon contaminant removal (McEvoy, J. P.; Foord, J. S. *Electrochim. Acta* 2005, 50, 2933). The cyclic voltammograms suggest that the number of active sites for Fe(CN)$_6^{3-/4-}$ oxidation created via alumina polishing is independent of the crystal face.

Figure 17:
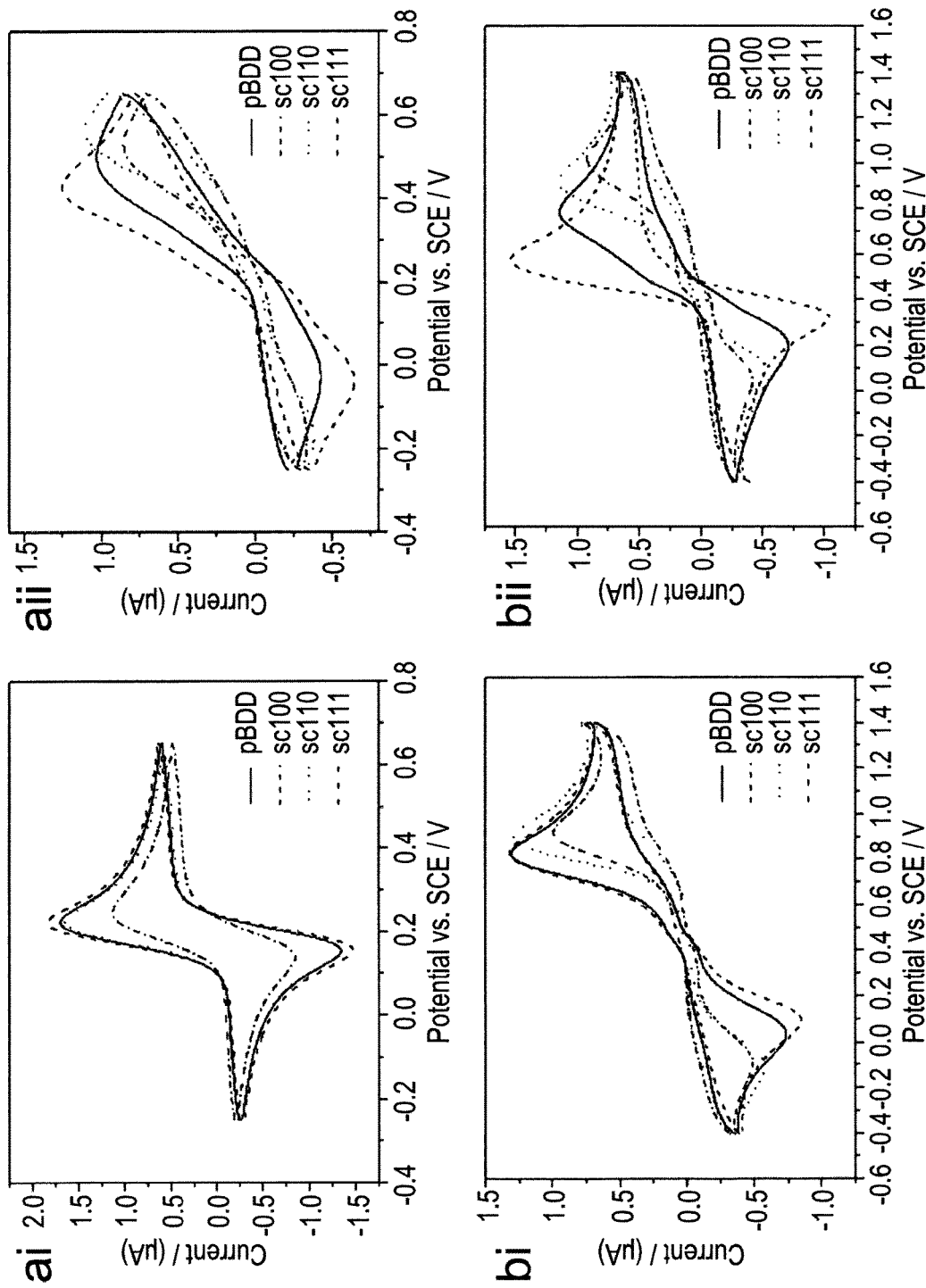
FIG. 17(a) shows cyclic voltammograms for the oxidation of 1 mM $Fe(CN)_6^{3-/4-}$ in 0.1M $KNO_3$ at metallically doped pBDD, {100}, {110} and {111} single crystal BDD, where (i) the diamond is oxygen-terminated via acid boiling and subsequent alumina polishing, and (ii) the diamond is oxygen-terminated via acid boiling and subsequent anodic polarisation for 60 seconds at 3 V versus a saturated calomel electrode in 0.1M $H_2SO_4$.
FIG. 17(b) shows cyclic voltammograms for the oxidation of 1 mM $Fe^{2+/3+}$ in 0.1M $HClO_4$ at a scan rate of 100 mV $s^{-1}$ at the 1 mm diameter BDD disc electrodes, where (i) the diamond is oxygen-terminated via acid boiling and subsequent alumina polishing, and (ii) the diamond is oxygen-terminated via acid boiling and subsequent anodic polarisation for 60 seconds at 3 V versus a saturated calomel electrode in 0.1M $H_2SO_4$.

In order to investigate why oxygen-terminated BDD is most often observed to have slow electron transfer kinetics for this species, all four electrodes was subjected to the most common method of oxygen-termination, anodic polarisation. FIG. 17(aii) shows cyclic voltammograms for the oxidation of 1 mM Fe(CN)$_6^{3-/4-}$ in 0.1M KNO$_3$ at metallically doped pBDD, {100}, {110} and {111} single crystal BDD, where the diamond is oxygen-terminated via acid boiling and subsequent anodic polarisation for 60 s at 3 V vs. SCE in 0.1M H$_2$SO$_4$. A dramatic increase in the $\Delta E_p$ values is seen for all diamond electrodes when the surface is terminated in this way, with the 100 surface having the smallest value of 413 mV, followed by the polycrystalline diamond with 500 mV separation. The {110} and {111} surfaces exhibit similar $\Delta E_p$ values, larger than that of {100}. The cyclic voltammograms show that the anodic pre-treatment reduces the number of active sites for Fe(CN)$_6^{3-/4-}$ oxidation and does this via a mechanism which is specific to the diamond crystal face. It is documented that while the oxygen functional groups at the {110} and {111} surfaces are expected to be the same, i.e. C—OH groups, those at the {100} surface are likely to take a different form, i.e. C—O—C or C=O (Nebel, C. E., Ristein, J. *Thin-Film Diamond II*; Elsevier Academic Press, 2004; Vol. 77). This could explain the trend in the peak to peak separations, with the polycrystalline surface having a mixture of the two types of functional groups.

Investigations of the classic inner-sphere redox couple $Fe^{2+/3+}$, at $sp^2$ carbon electrodes, have shown that electron transfer kinetics can be strongly affected by the electrode surface, most notably the presence of oxides (Ohnishi, K.; Einaga, Y.; Notsu, H.; Terashima, C.; Rao, T. N.; Park, S. G.; Fujishima, A. *Electrochem. Solid-State Lett.* 2002, 5, D1). FIG. 17(*b*) shows cyclic voltammograms for the oxidation of 1 mM $Fe^{2+/3+}$ in 0.1M $HClO_4$ at a scan rate of 100 mV $s^{-1}$ at the 1 mm diameter BDD disc electrodes for: (i) alumina polished; and (ii) anodised surfaces. The $\Delta E_p$ values for this system at alumina polished surfaces where seen to range from 830 mV for the {100} face to 885 mV for the {110} face, indicating a quasi-reversible system. These are slightly larger than the values observed by others for as-deposited ($\Delta E_p$ of 837 mV) pBDD. However, upon anodic pretreatment, the $\Delta E_p$ values were shown to decrease for all diamond electrodes, as shown in FIG. 17(*bii*). Most notably the {100} face peak to peak separation was found to be 234 mV. Again, the polycrystalline sample was found to be a combination of the {100} and {110}/{111} surface affects.

In a similar approach, as with $Fe(CN)_6^{3-/4-}$, it has been suggested that a specific oxygen containing functional group affects the electron transfer kinetics. In this case, carbonyls are responsible for facilitating $Fe^{2+/3+}$ electron transfer, as has been previously suggested for glassy carbon electrodes. As mentioned above, the dominant oxygen functional groups on a {100} diamond face are expected to be C=O or C—O—O, whereas for the {110} and {111} faces, C—OH groups are likely to dominate. The cyclic voltammograms presented would imply that upon anodic polarisation, C=O groups are generated at the {100} diamond face, thus facilitating $Fe^{2+/3+}$ electron transfer. However, these groups are not created to such an extent at the {110}, {111} or polycrystalline surfaces, leaving a low density of active sites. This work would suggest that by use of single crystal diamond, a high number of specific active site could be created in order to facilitate electron transfer to certain redox species by using {100} oriented single crystal material.

Use of Boron Doped Diamond Materials as a Hydrogen Sulphide Sensor $H_2S$ is a colourless, flammable and toxic gas at room temperature and 1 atmosphere (i.e. 101.3 kPa) pressure. It has a rotten egg odour and acts upon the central nervous system (narcosis) with exposure limits of 10 ppm over a period of 8 hours. 100 ppm exposure causes headaches and at 300 ppm $H_2S$ is considered immediately hazardous with a lethal concentration value $LC_{50}$ of 713 ppm. $H_2S$ is a weak acid, a reducing agent, is air oxidized, and absorbs on metals (corrosive). Its solubility depends on temperature, pressure, agitation, phase (oil/water), and pH. $H_2S$ has a high partition coefficient between liquid and vapour, i.e. 1 ppm in the liquid phase can give rise to >50 ppm concentration in a vapour space.

$H_2S$ dissolved in $H_2O$ (at 25° C.) gives the following products:

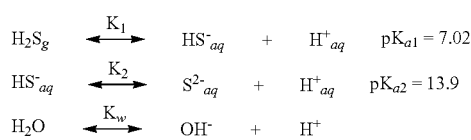

Electrochemically, it is possible to detect $HS^-$ or $S^{2-}$, dependant on the pH of the solution. Hence, it is possible to mimic the presence of $H_2S$ in solution by using a sodium salt (i.e. NaHS or $Na_2S$):

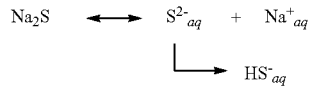

Sulfide ($S^{2-}$) at pH levels less than 13.9 will convert to sulphite (HS). Oxidation of sulphite gives:

$HS^-$ goes to $S°$ (solid)$+H^++e^-$

The most popular techniques for detection of $H_2S$ in water include spectroscopy, chromatography, and electrochemistry. Classic methods for detection of $H_2S$ in water include titration of sulphide with iodine or methylene blue which both comprise indirect detection of $H_2S$. The present inventors have devised a strategy comprising direct oxidation of $H_2S$ in water using boron doped diamond materials as described herein. In addition to health and environmental applications, this method will also be applicable to detection of sulphur content for oil and gas applications where sulphur content affects the quality of oil and gas fuels.

Experiments have been performed to assess the effectiveness of boron doped diamond materials for the detection of $H_2S$ (specifically HS) at pH 10. All solutions were degassed and an electrochemical cell was used comprising a Teflon™ lid, a stirrer and stirring bar, a platinum wire counter electrode and an SCE reference electrode. A stock solution was prepared comprising 10 mM $Na_2S$ in 25 mM NaOH in a degassed conical flask sealed with a rubber stopper. Sample solutions were then prepared by addition of increasing volumes of stock solution to 10 mL of sodium tetraborate buffer (pH 10, no added salt).

Figure 18:
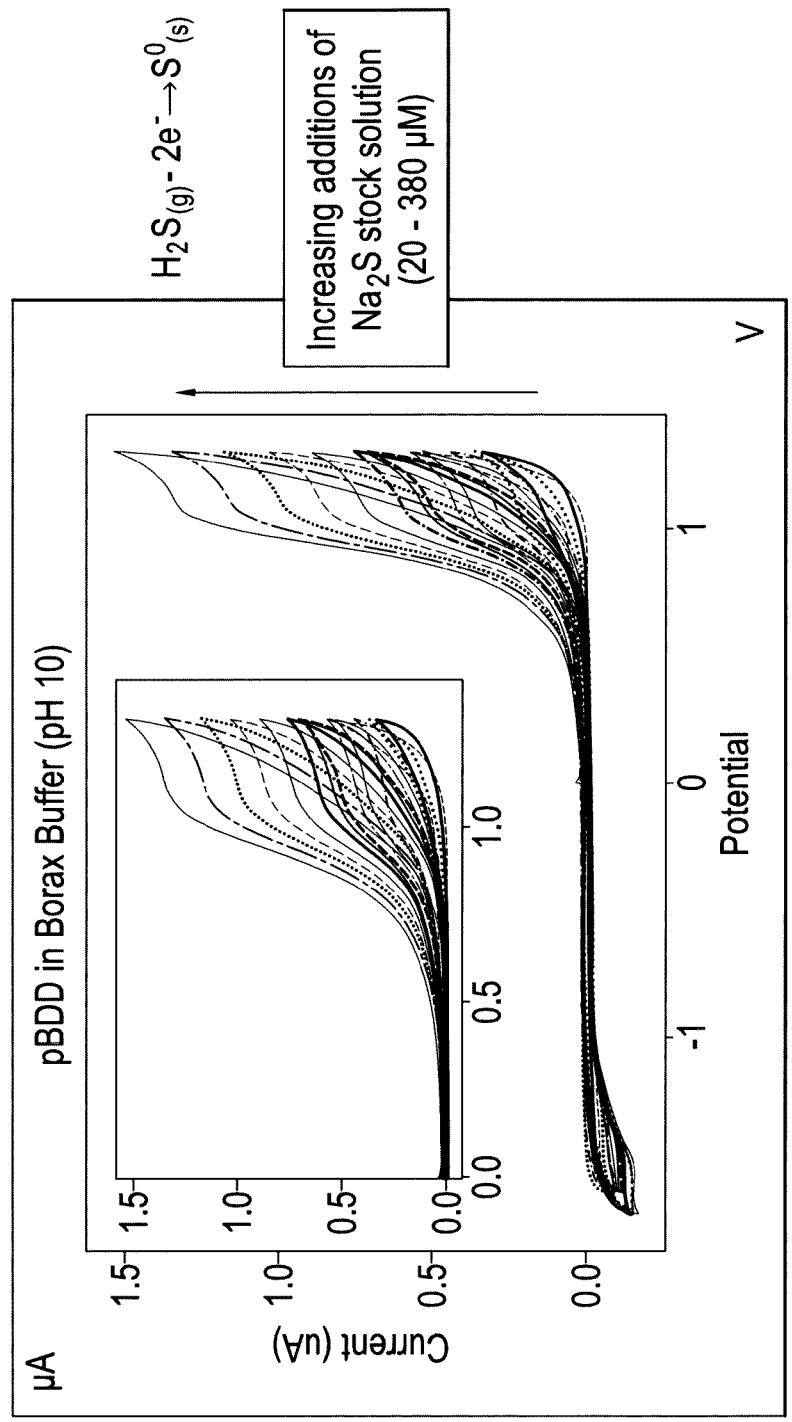
FIG. 18 shows cyclic voltammograms illustrating the precipitation of sulphur (in the cathodic window from reduction of HS) and detection of $HS^-$ (in the anodic window) in aqueous solution at pH 10 using a boron doped diamond electrode according to the present invention (the inset shows a portion of the voltammograms in more detail)
Figure 19:
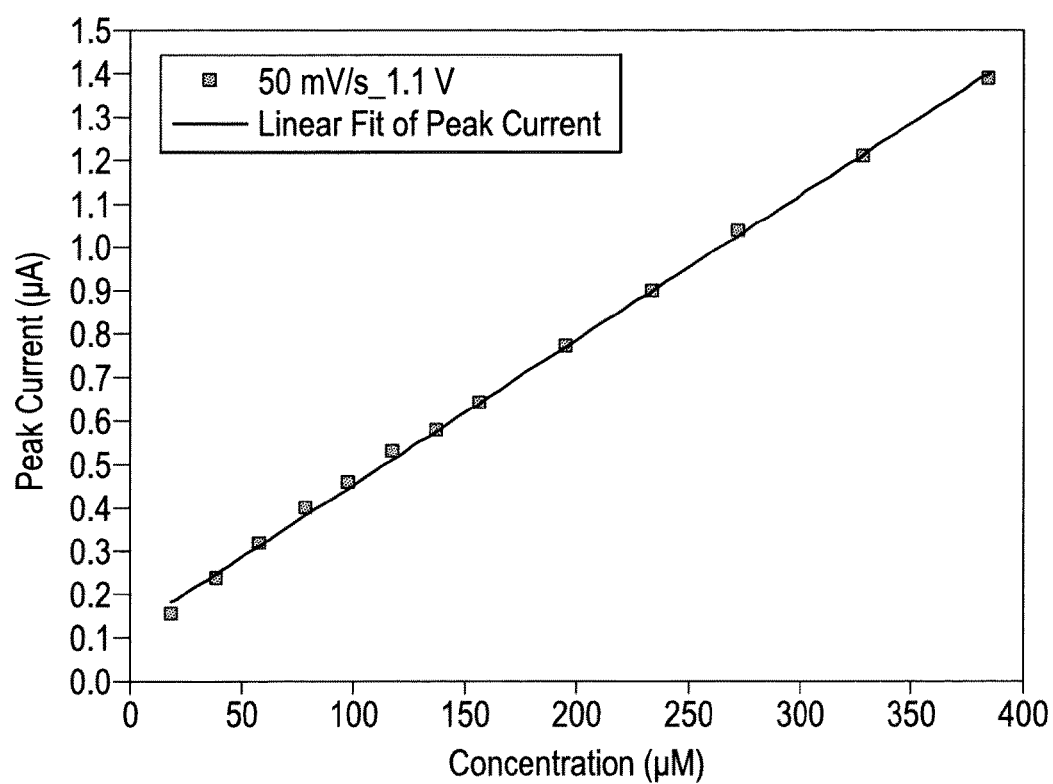
FIG. 19 shows a plot of peak current vs sulphide concentration from the data of FIG. 18 illustrating a linear relationship down to very low concentrations.
Figure 20:
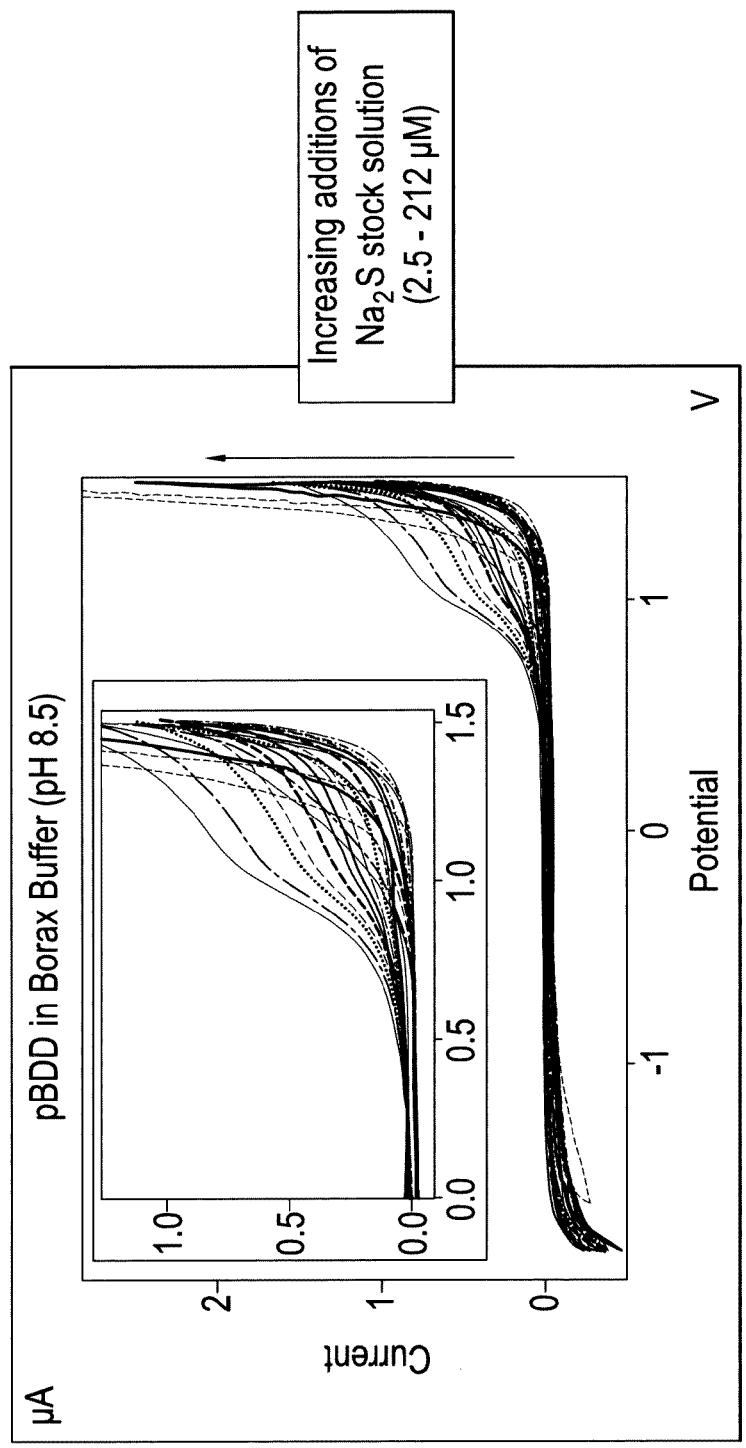
FIG. 20 shows cyclic voltammograms illustrating the precipitation of sulphur (in the cathodic window from reduction of HS) and detection of $HS^-$ (in the anodic window) in aqueous solution at pH 8.5 using a boron doped diamond electrode according to the present invention (the inset shows a portion of the voltammograms in more detail)
Figure 21:
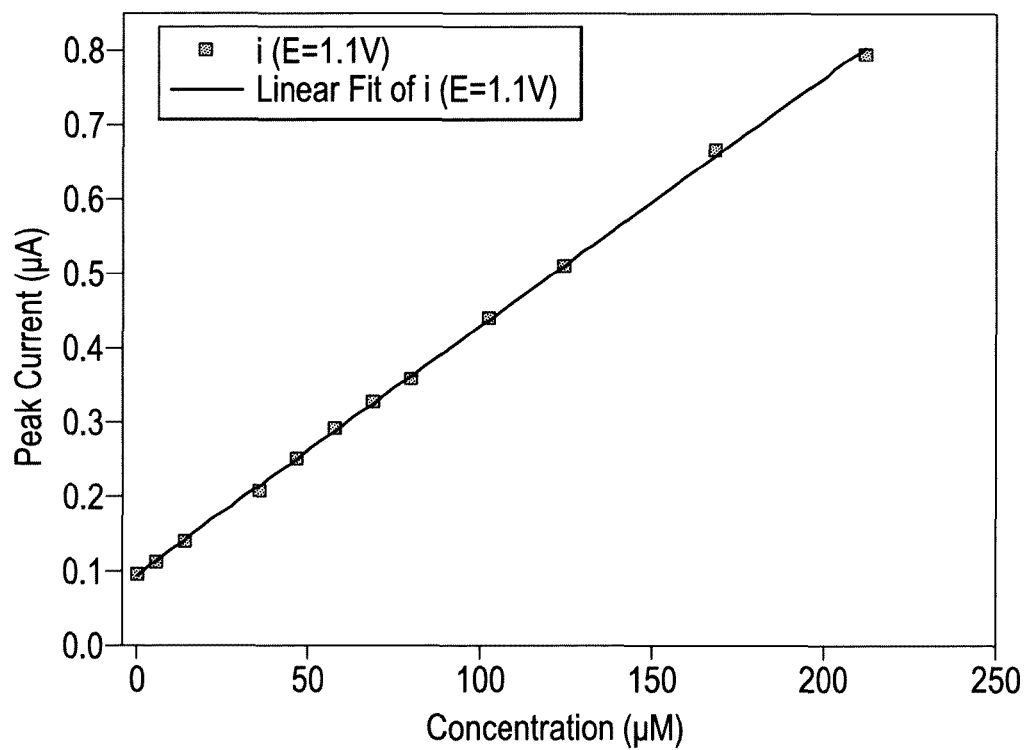
FIG. 21 shows a plot of peak current vs sulphide concentration from the data of FIG. 20 illustrating a linear relationship down to very low concentrations.

Using a boron doped diamond electrode according to an embodiment of the present invention as the working electrode of the aforementioned electrochemical cell it was found to be possible to reproducibly precipitate sulphur directly onto the working electrode and thus directly measure $HS^-$ content in aqueous solution down to much lower concentrations than previously reported. Results are illustrated in FIGS. 18 and 19. FIG. 18 illustrates voltammograms obtained for varying concentrations of $Na_2S$ (the insert showing an end portion of the voltammograms in more detail) while FIG. 19 shows a plot of peak current versus concentration of $HS^-$ indicating a linear increase in current response with increasing $HS^-$ concentration. Previously, Lawrence et al. (Electroanalysis, 2002, 14(7-8), 499-504) reported electrochemically detecting $HS^-$ in aqueous solution from 1000 μM down to 200 μM. However, it is believed that Lawrence et al. were unable to detect lower concentrations due to the use of a working electrode material with a shorter solvent window than the materials described herein or alternatively a higher background current. In contrast, using the boron doped diamond materials as described herein it was possible to detect $HS^-$ in aqueous solution at a concentration below 200 μM, 175 μM, 150 μM, 125 μM, 100 μM, 75 μM, 50 μM, 40 μM, 30 μM, 20 μM, 10 μM, 5 μM and down to at least 2 μM at pH 10 while exhibiting a linear response of peak current to $HS^-$ concentration. That is, the materials of the present invention enabled a one to two orders of magnitude improvement in the sensitivity for electrochemical detection of $HS^-$ in aqueous solution when compared to the lowest value reported in the prior art. The procedure was repeated at pH 8.5 and showed the same linear response between peak current and HS⁻ concentration. These results are illustrated in FIGS. 20 and 21 (FIG. 20 illustrates voltammograms obtained for varying concentrations of $Na_2S$ while FIG. 21 shows a plot of peak current versus concentration of HS⁻ indicating a linear increase in current response with increasing HS⁻ concentration down to a concentration of approximately 2 μM).

Furthermore, the effect of adding potentially interfering species such as $KNO_3$, NaCl, and sulphate ($SO_4^{2-}$) was investigated and it was found that these species had no effect on the ability to detect HS⁻ as described above.

As such, it has been shown that the materials of the present invention provide a significant improvement in the ability to detect hydrogen sulphide at very low concentrations. It is believed that further improvements in sensitivity can be made by fabricating micro-band electrode structures using the boron doped diamond materials described herein. It is also envisaged that the boron doped diamond materials described herein will show corresponding improvements in selectively and sensitivity for other target species such as heavy metals (relevant to environmental applications and to oil and gas applications) and organic species (relevant to medical diagnostics and pharmaceutical applications).

While this invention has been particularly shown and described with reference to preferred embodiments, it will be understood to those skilled in the art that various changes in form and detail may be made without departing from the scope of the invention as defined by the appendant claims.

The invention claimed is:

1. A boron doped synthetic diamond material which has the following characteristics:
   a solvent window meeting one or both of the following criteria as measured by sweeping a potential of the boron doped synthetic diamond material with respect to a saturated calomel reference electrode in a solution containing only deionised water and 0.1M $KNO_3$ as a supporting electrolyte at pH 6:
      the solvent window extends over a potential range of at least 4.1 V wherein end points of the potential range for the solvent window are defined when anodic and cathodic current density measured at the boron doped synthetic diamond material reaches 38 mA cm⁻²; and
      the solvent window extends over a potential range of at least 3.3 V wherein end points of the potential range for the solvent window are defined when anodic and cathodic current density measured at the boron doped synthetic diamond material reaches 0.4 mA cm⁻²;
   a peak-to-peak separation $\Delta E_p$ (for a macroelectrode) or a quartile potential $\Delta E_{3/4-1/4}$ (for a microelectrode) of no more than 70 mV as measured by sweeping a potential of the boron doped synthetic diamond material at a rate of 100 mV s⁻¹ with respect to a saturated calomel reference electrode in a solution containing only deionised water, 0.1M $KNO_3$ supporting electrolyte, and 1 mM of $FcTMA^+$ or $Ru(NH_3)_6^{3+}$ at pH 6; and
   a capacitance of no more than 10 μF cm⁻² as measured by sweeping a potential of the boron doped synthetic diamond material with respect to a saturated calomel reference electrode between 70 mV and −70 mV in a solution containing only deionised water and 0.1M $KNO_3$ supporting electrolyte at pH 6, measuring resultant current, subtracting a current value at 0 V when sweeping towards negative potentials from a current value at 0 V when sweeping towards positive potentials, dividing the subtracted current value by 2, and then dividing the result by an area (cm²) of the boron doped synthetic diamond material and by a rate at which the potential is swept (V s⁻¹) to give a value for capacitance in F cm⁻²,
   wherein at least a portion of an exposed surface layer of the boron doped synthetic diamond material comprises boron doped synthetic diamond material having a boron content in a range 7×10²⁰ boron atoms cm⁻³ to 7×10²¹ boron atoms cm⁻³, and
   wherein the boron doped diamond material does not exhibit non-diamond carbon peaks in a Raman spectrum of the boron doped diamond material.

2. A boron doped synthetic diamond material according to claim 1, wherein the solvent window extends over at least a potential range of 4.3 V wherein end points of the potential range for the solvent window are defined when anodic and cathodic current density measured at the boron doped synthetic diamond material reaches 38 mA cm⁻².

3. A boron doped synthetic diamond material according to claim 2, wherein the solvent window extends over at least a potential range of −2.1V to +2.2V.

4. A boron doped synthetic diamond material according to claim 1, wherein the solvent window extends over at least a potential range of 3.4 V wherein end points of the potential range for the solvent window are defined when anodic and cathodic current density measured at the boron doped synthetic diamond material reaches 0.4 mA cm⁻².

5. A boron doped synthetic diamond material according to claim 1, wherein $\Delta E_p$ or $\Delta E_{3/4-1/4}$ is no more than 66 mV.

6. A boron doped synthetic diamond material according to claim 1, wherein the capacitance is no more than 8 μF cm⁻².

7. A boron doped synthetic diamond material according to claim 1, wherein at least 50% of an exposed surface layer comprises boron doped synthetic diamond material having a boron content in a range 7×10²⁰ boron atoms cm⁻³ to 7×10²¹ boron atoms cm⁻³.

8. A boron doped synthetic diamond material according to claim 1, wherein the exposed surface layer comprises boron doped synthetic diamond material having a boron content of no more than 3×10²¹ boron atoms cm⁻³.

9. A boron doped synthetic diamond material according to claim 1, wherein the boron doped synthetic diamond material is a single crystal boron doped synthetic diamond material.

10. A boron doped synthetic diamond material according to claim 9, wherein the single crystal boron doped synthetic diamond material comprises a capping layer having a boron content in a range 7×10²⁰ boron atoms cm⁻³ to 7×10²¹ boron atoms cm⁻³ and a support layer having a lower boron content than the capping layer.

11. A boron doped synthetic diamond material according to claim 10, wherein the support layer has a boron content of at least 5×10¹⁸ boron atoms cm⁻³.

12. A boron doped synthetic diamond material according to claim 9, wherein a majority volume of at least 50% of the single crystal boron doped synthetic diamond material has a boron content in a range 7×10²⁰ boron atoms cm⁻³ to 7×10²¹ boron atoms cm⁻³.

13. A boron doped synthetic diamond material according to claim 9, wherein an exposed surface of the single crystal boron doped synthetic diamond material comprises no more than 5% by area of crystallographic defects observable by visible microscopy at a magnification of up to ×100.

14. A boron doped synthetic diamond material according to claim 1, wherein the boron doped synthetic diamond material is a polycrystalline boron doped synthetic diamond material.

\* \* \* \* \*